US010070929B2

(12) United States Patent
Tanji

(10) Patent No.: US 10,070,929 B2
(45) Date of Patent: Sep. 11, 2018

(54) SURGICAL OPERATION SUPPORT SYSTEM, SURGICAL OPERATION SUPPORT APPARATUS, SURGICAL OPERATION SUPPORT METHOD, SURGICAL OPERATION SUPPORT PROGRAM, AND INFORMATION PROCESSING APPARATUS

(71) Applicant: Atsushi Tanji, Tokyo (JP)

(72) Inventor: Atsushi Tanji, Tokyo (JP)

(*) Notice: Subject to any disclaimer, the term of this patent is extended or adjusted under 35 U.S.C. 154(b) by 290 days.

(21) Appl. No.: 14/897,964

(22) PCT Filed: Jun. 11, 2014

(86) PCT No.: PCT/JP2014/065447
§ 371 (c)(1),
(2) Date: Dec. 11, 2015

(87) PCT Pub. No.: WO2014/200016
PCT Pub. Date: Dec. 18, 2014

(65) Prior Publication Data
US 2016/0143699 A1 May 26, 2016

(30) Foreign Application Priority Data
Jun. 11, 2013 (JP) ................................ 2013-123209

(51) Int. Cl.
*A61B 5/00* (2006.01)
*A61B 34/20* (2016.01)
(Continued)

(52) U.S. Cl.
CPC .... *A61B 34/20* (2016.02); *A61B 2017/00526* (2013.01); *A61B 2034/108* (2016.02);
(Continued)

(58) Field of Classification Search
CPC .......... A61B 34/20; A61B 2017/00526; A61B 2090/3983; A61B 2034/108;
(Continued)

(56) References Cited

U.S. PATENT DOCUMENTS 6,241,735 B1 6/2001 Marmulla
2005/0228266 A1* 10/2005 McCombs ............. A61B 34/74
600/414

(Continued)

FOREIGN PATENT DOCUMENTS

JP 2001-507614 A 6/2001
JP 2003-339725 A 12/2003
(Continued)

OTHER PUBLICATIONS

Japanese Office Action dated Aug. 17, 2017 for Japanese Application 2016-197895.
(Continued)

*Primary Examiner* — Joel Lamprecht
(74) *Attorney, Agent, or Firm* — Ladas & Parry LLP

(57) ABSTRACT

A system of this invention is directed to a surgical operation support system that supports determination of an appropriate disposition of a bone in a living body during surgery. The surgical operation support system includes a storage that stores 3D data of a first target bone that is one of two divided surgery target bones and 3D data of a reference bone partially overlapping the first target bone in association with position data of a first marker fixed to the first target bone, and stores 3D data of a second target bone that is the other of the two divided surgery target bones in association with position data of a second marker fixed to the second target bone, an image capturer that captures the first marker fixed to the first target bone and the second marker fixed to the second target bone, and a display that changes display in
(Continued)

accordance with a change in relative positions of the first marker and the second marker using the data stored in the storage such that the target position of the second marker with respect to the first marker when the second target bone overlaps the reference bone can be grasped.

15 Claims, 35 Drawing Sheets

(51) Int. Cl.
*A61B 90/50* (2016.01)
*A61B 90/00* (2016.01)
*A61B 34/10* (2016.01)
*A61B 17/00* (2006.01)

(52) U.S. Cl.
CPC .............. *A61B 2034/2055* (2016.02); *A61B 2034/2057* (2016.02); *A61B 2034/2065* (2016.02); *A61B 2090/364* (2016.02); *A61B 2090/365* (2016.02); *A61B 2090/367* (2016.02); *A61B 2090/372* (2016.02); *A61B 2090/3983* (2016.02); *A61B 2090/3991* (2016.02); *A61B 2090/502* (2016.02)

(58) Field of Classification Search
CPC ........ A61B 2090/367; A61B 2090/365; A61B 2090/372; A61B 2090/502; A61B 2034/2055

See application file for complete search history.

(56) References Cited

U.S. PATENT DOCUMENTS

2006/0015018 A1 1/2006 Jutras et al.
2006/0176242 A1 8/2006 Jaramaz et al.

FOREIGN PATENT DOCUMENTS

| JP | 2008-526422 A | 7/2008 |
| JP | 2009-172124 A | 8/2009 |
| WO | 2006/075331 A2 | 7/2006 |

OTHER PUBLICATIONS

J-PlatPat English abstract of JP 2003-339725 A.
International Search Report dated Sep. 10, 2014 for Application No. PCT/JP2014/065447 with English translation.
J-PlatPat partial English translation of JP 2008-526422 A.
J-PlatPat partial English translation of JP 2001-507614 A.
J-PlatPat English abstract of JP 2009-172124 A.

\* cited by examiner

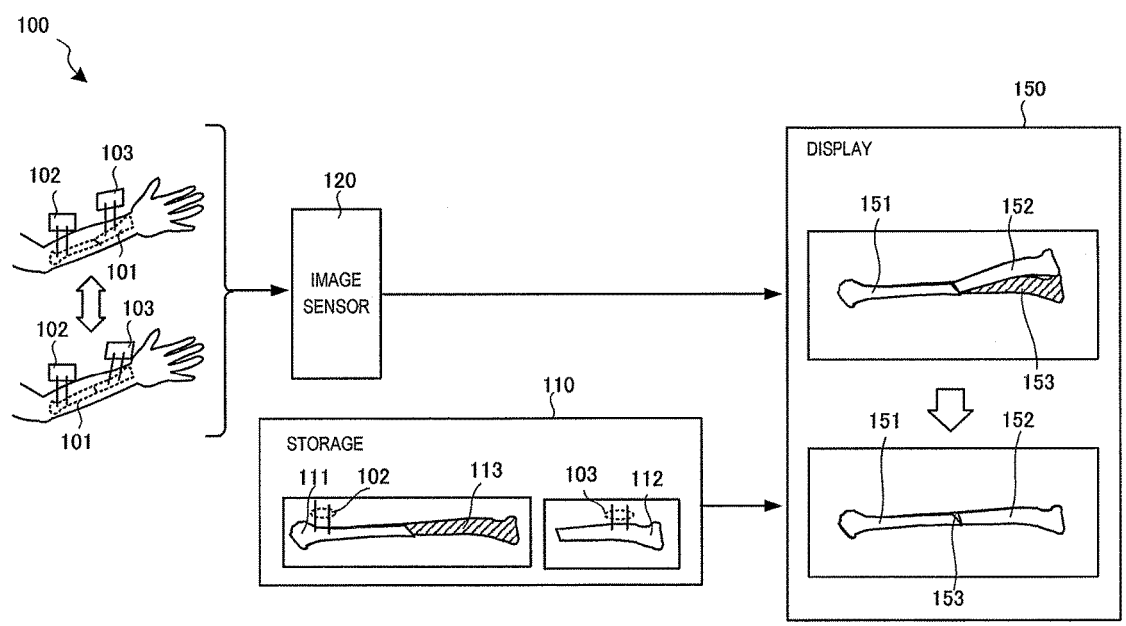
F I G. 1

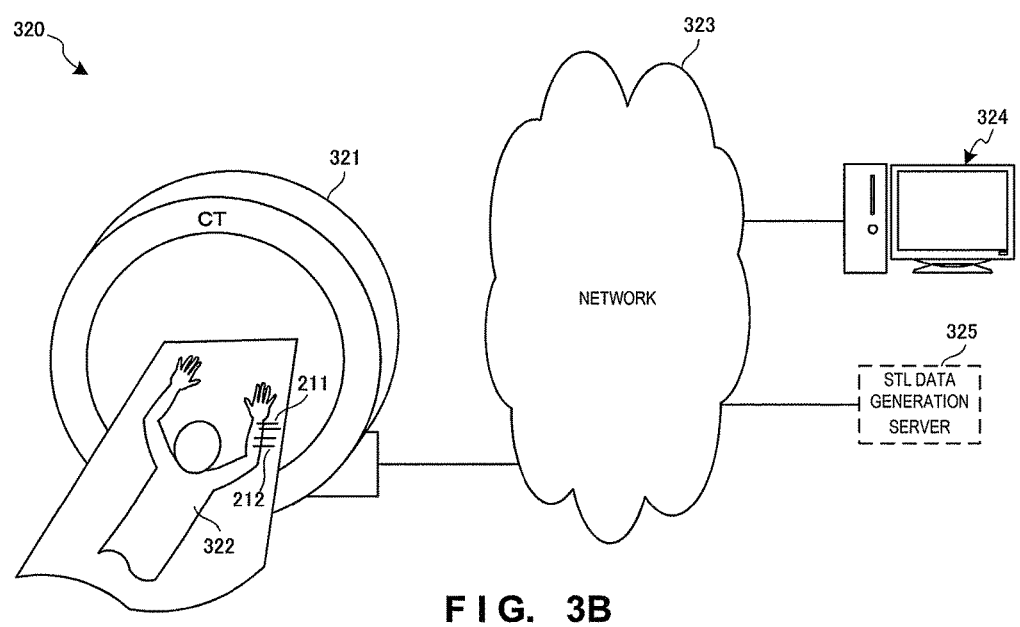
F I G. 3B

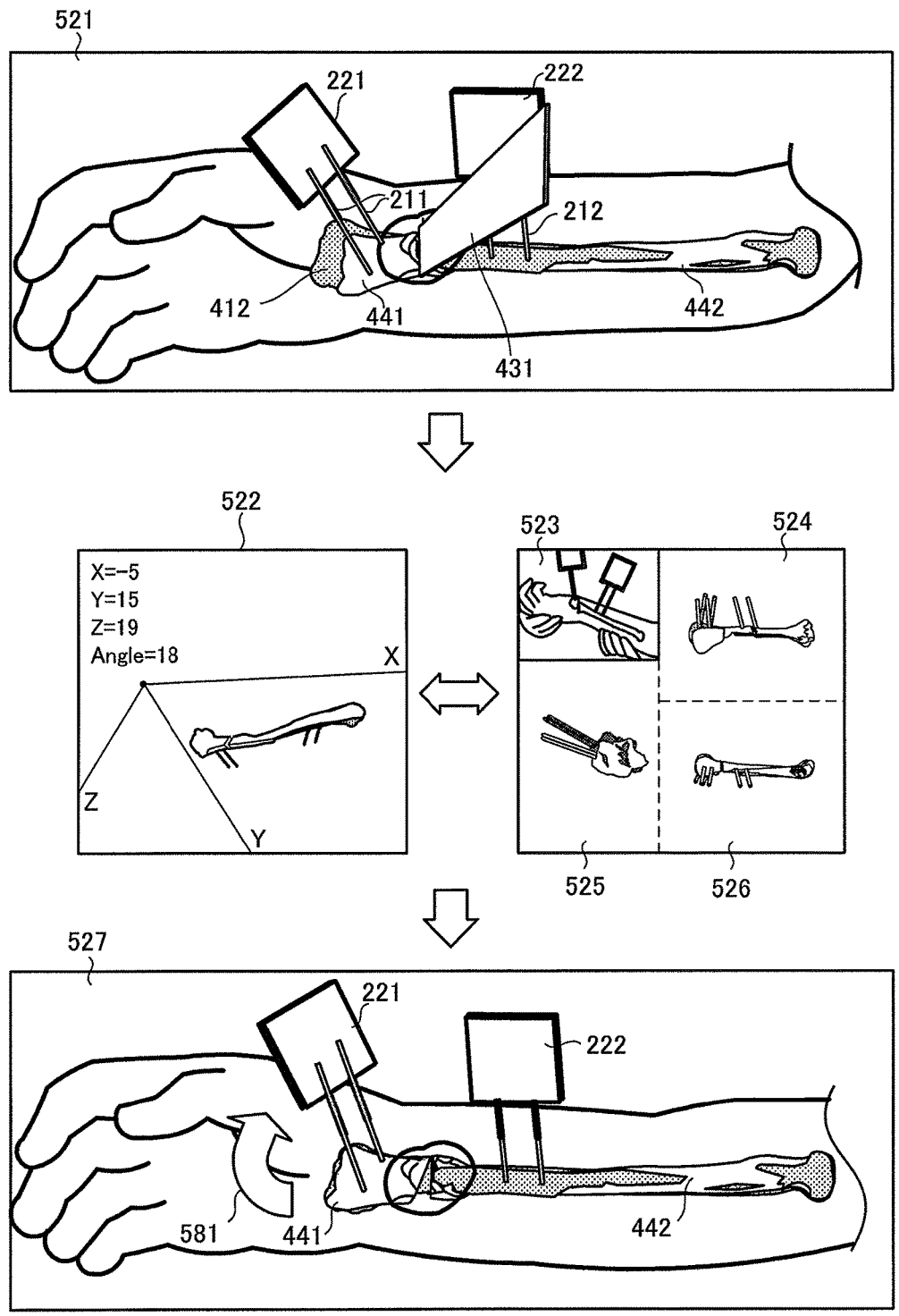
F I G. 5B

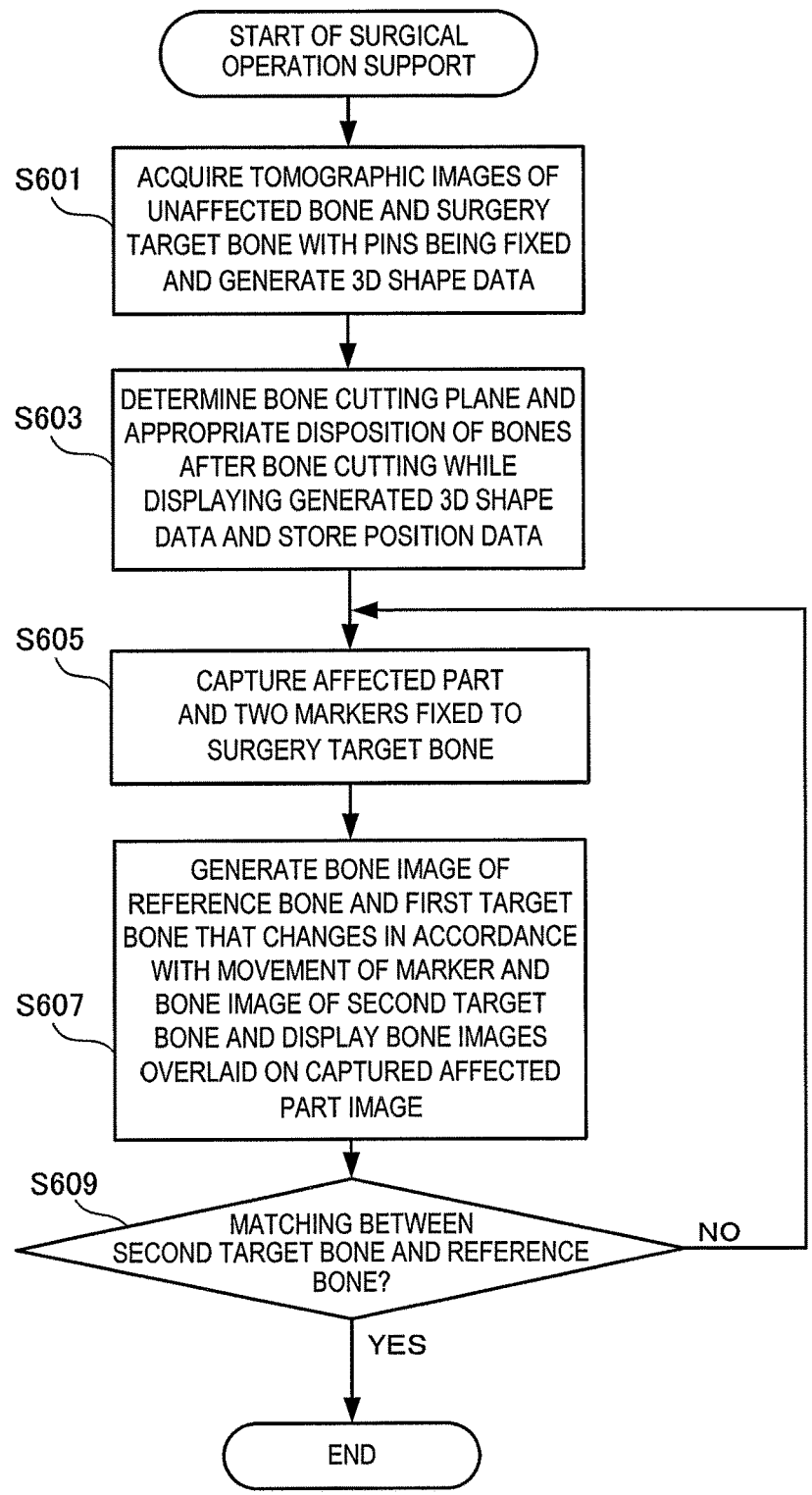
F I G. 6

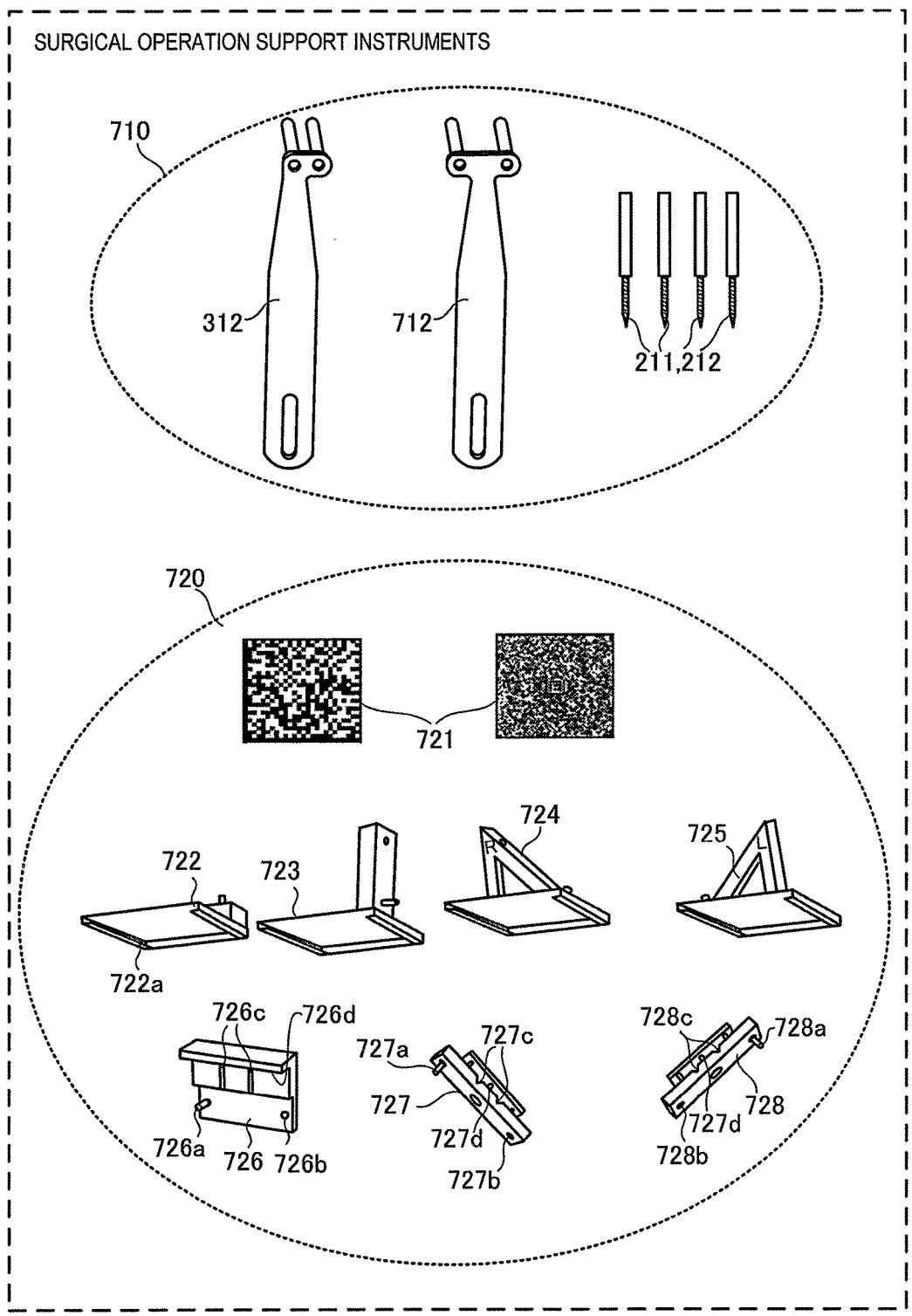
F I G. 7

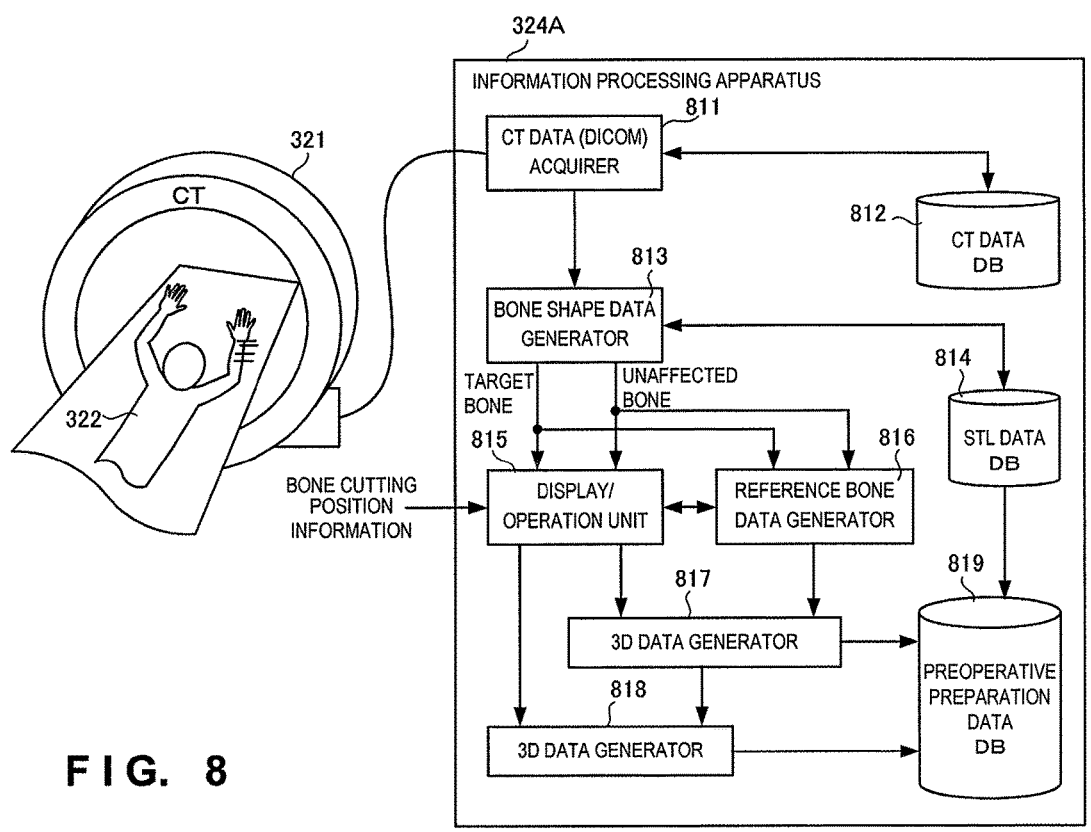
F I G. 8

814

| IMAGE ID | CT DATA ACQUISITION DATE / TIME | PATIENT NAME | AFFECTED PART | SYMPTOM | CT DATA | STL DATA | STL DATA GENERATION SOURCE | ... |
|---|---|---|---|---|---|---|---|---|
| | | | | | | | | |
| | | | | | | | | |
| | | | | | | | | |
| ⋮ | | | | | | | | |

1001, 1002, 1003, 1004, 1005, 1006, 1007, 1008

F I G. 10

819

| PATIENT NAME | AFFECTED PART | SYMPTOM | 3D DATA OF FIRST TARGET BONE | 3D POSITION DATA OF FIRST MARKER SUPPORT INSTRUMENT | 3D DATA OF REFERENCE BONE | 3D DATA OF SECOND TARGET BONE | 3D POSITION DATA OF SECOND MARKER SUPPORT INSTRUMENT | ... |
|---|---|---|---|---|---|---|---|---|
| | | | | | | | | |
| | | | | | | | | |
| | | | | | | | | |
| ⋮ | | | | | | | | |

- 1101: PATIENT NAME
- 1102: AFFECTED PART
- 1103: SYMPTOM
- 1104: (3D DATA OF FIRST TARGET BONE, 3D POSITION DATA OF FIRST MARKER SUPPORT INSTRUMENT, 3D DATA OF REFERENCE BONE)
- 1105: (3D DATA OF SECOND TARGET BONE, 3D POSITION DATA OF SECOND MARKER SUPPORT INSTRUMENT)

F I G. 11

1200

| 1201 | 1202 | 1203 | 1204 | 1205 | 1206 |
|---|---|---|---|---|---|
| REFERENCE BONE IMAGE ID | PATIENT NAME | AFFECTED PART | SYMPTOM | UNAFFECTED BONE STL DATA | REFERENCE BONE STL DATA |
| | | | | | |
| | | | | | |
| | | | | | |
| ⋮ | | | | | |

F I G. 12

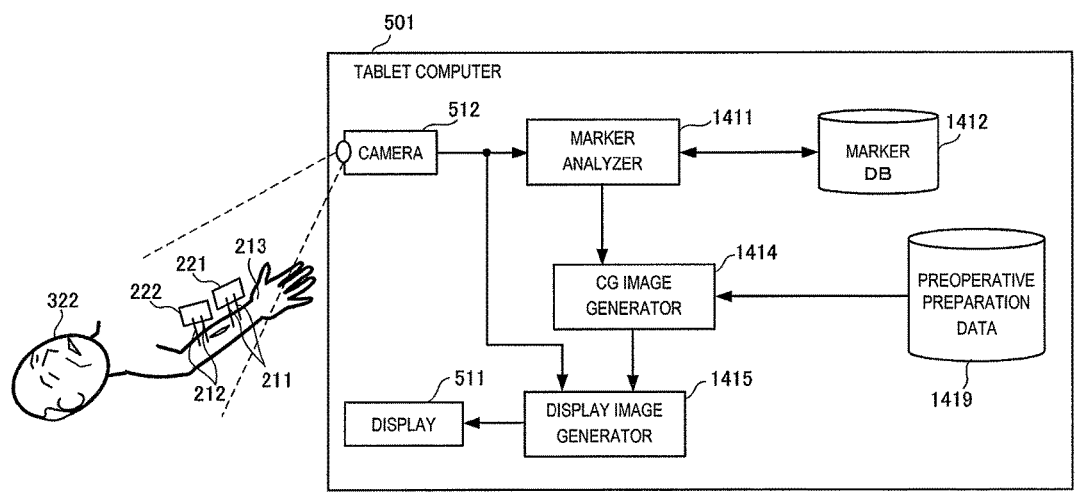
F I G. 14

1412

| MARKER ID | MATRIX DATA | MARKER SHAPE | MARKER SIZE | ... |
|---|---|---|---|---|
|  |  |  |  |  |
|  |  |  |  |  |
| ⋮ |  |  |  |  |

FIG. 15

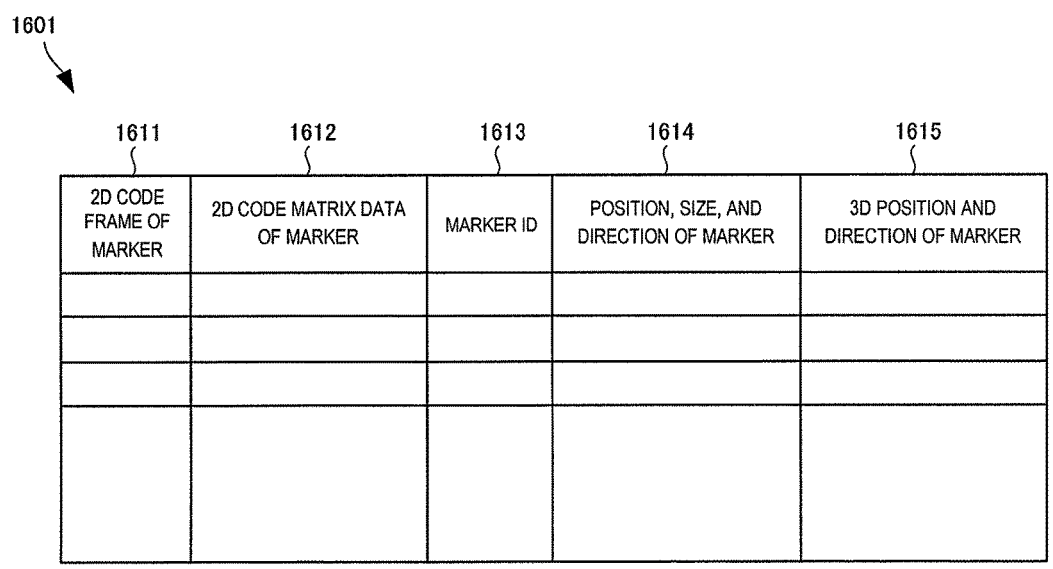
F I G. 16A

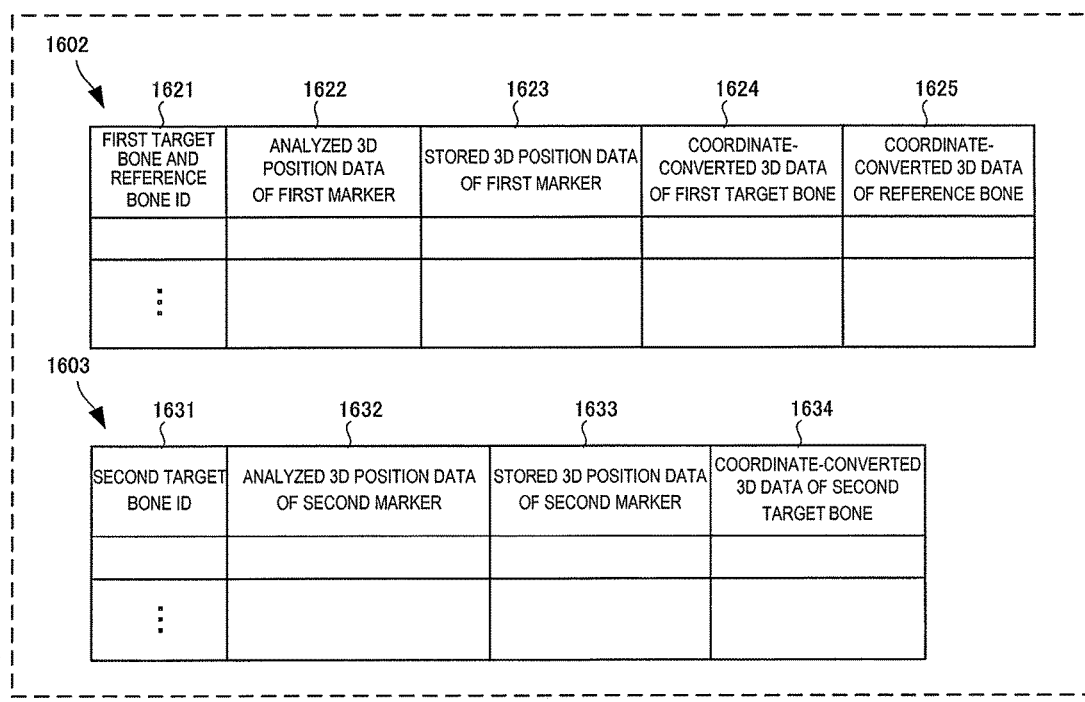
F I G. 16B

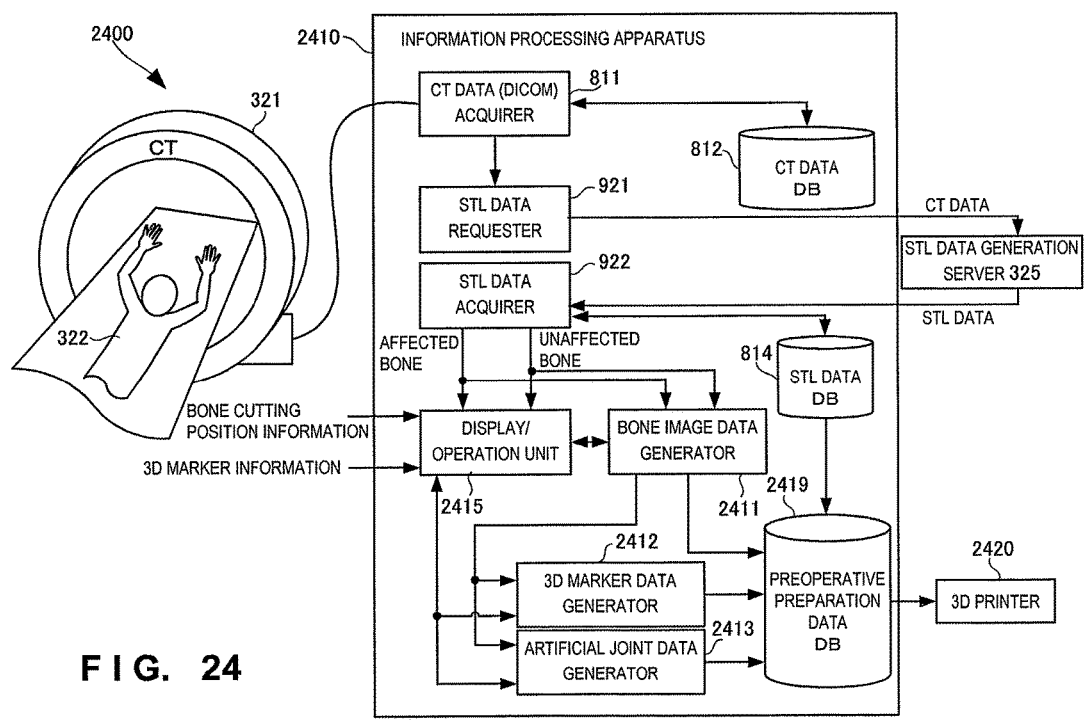
F I G. 24

| PATIENT NAME | AFFECTED PART | TECHNIQUE | PLANNING ITEM | 3D DATA |
|---|---|---|---|---|
| A | RIGHT ARM / ELBOW | ARTIFICIAL JOINT REPLACEMENT | 3D MARKER | 3D MARKER GENERATION DATA / MARKER PLACEMENT POSITION DATA |
| | | | BONE CUTTING PLANE, BONE HOLE | BONE CUTTING PLANE POSITION DATA / BONE HOLE POSITION DATA |
| | | | IMPLANT | IMPLANT GENERATION DATA / IMPLANT POSITION DATA |
| | | | ⋮ | |
| B | LEFT ARM / ELBOW | CORRECTIVE OSTEOTOMY FOR MALUNION | 3D MARKER | 3D MARKER GENERATION DATA / MARKER PLACEMENT POSITION DATA |
| | | | BONE CUTTING PLANE, BONE MOVING AMOUNT | BONE CUTTING PLANE POSITION DATA / BONE MOVING AMOUNT DATA |
| | | | ⋮ | |
| C | LEFT LEG / KNEE | OSTEOARTHRITIS | 3D MARKER | 3D MARKER GENERATION DATA / MARKER PLACEMENT POSITION DATA |
| | | | BONE RESECTION | BONE RESECTION RANGE DATA |
| | | | ⋮ | |
| ⋮ | | | | |

FIG. 25

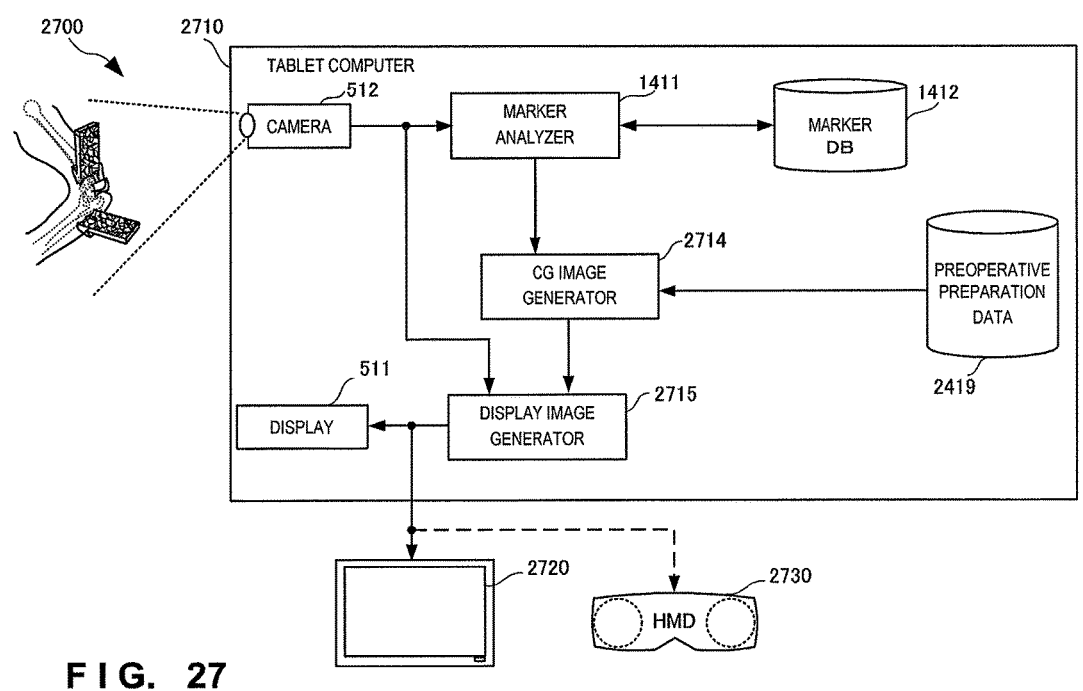
F I G. 27

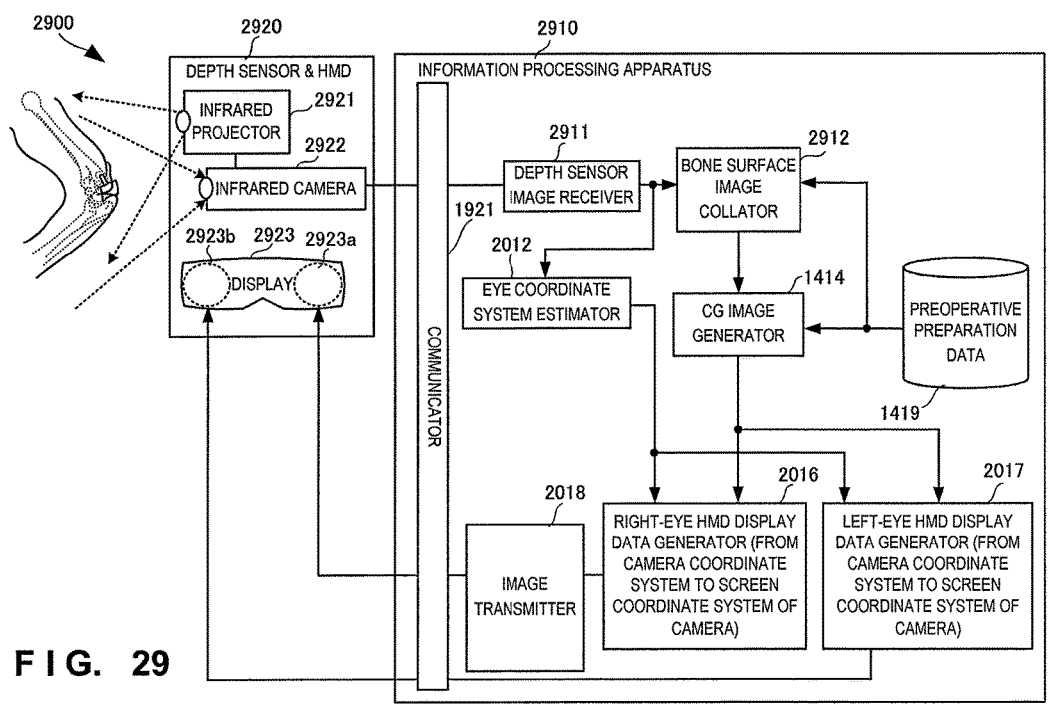
F I G. 29

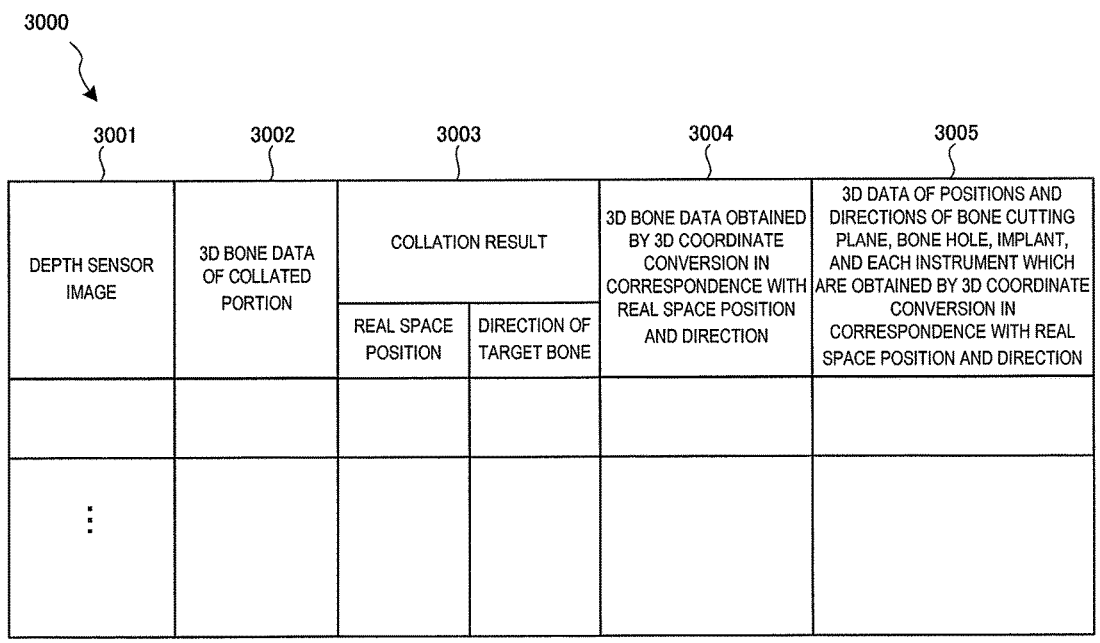
F I G. 30

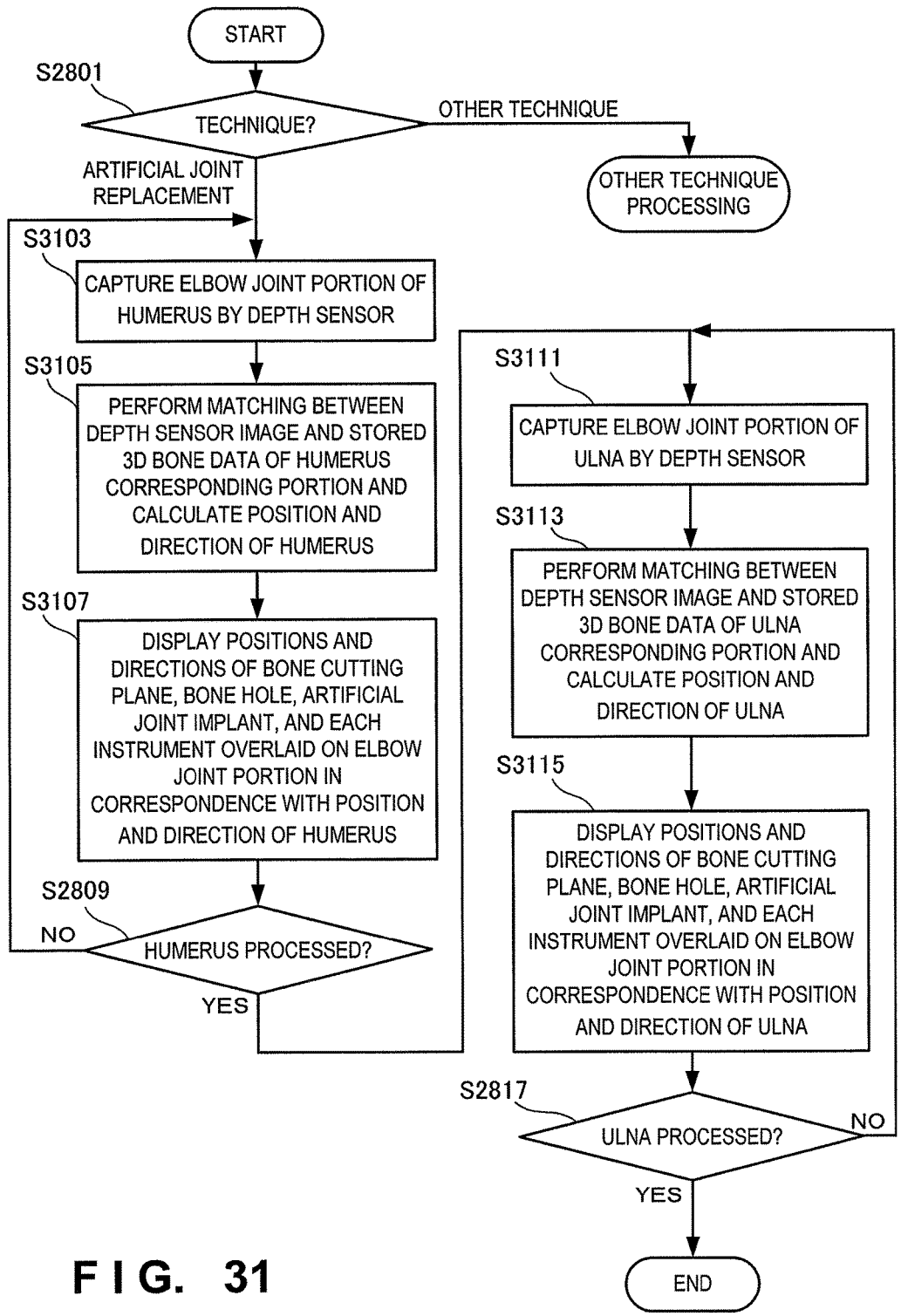
F I G. 31

SURGICAL OPERATION SUPPORT SYSTEM, SURGICAL OPERATION SUPPORT APPARATUS, SURGICAL OPERATION SUPPORT METHOD, SURGICAL OPERATION SUPPORT PROGRAM, AND INFORMATION PROCESSING APPARATUS

RELATED APPLICATION

This application is an application under 35 U.S.C. 371 of International Application No. PCT/JP2014/065447 filed on Jun. 11, 2014, the entire contents of which are incorporated herein by reference.

TECHNICAL FIELD

The present invention relates to a technique of supporting a surgical operation by image processing.

BACKGROUND ART

In the above-described technical field, patent literature 1 discloses a technique of attaching a marker indicating the position of the skull of a patient and capturing the marker, thereby automatically controlling the attachment position of a robot for surgery support. Non-patent literature 1 shows software that generates STL (Stereo Lithography) data of a 3D bone surface model from DICOM (Digital Imaging and Communication in Medicine) data that is a standard format of a medical image of CT/MRI or the like. Non-patent literature 2 shows software that simulates bone and joint surgery in advance using 3D bone surface model (STL) data.

CITATION LIST

Patent Literature

Patent literature 1: Japanese PCT National Publication No. 2008-526422

Non-Patent Literature

Non-patent literature 1: Simple bone model 3D data creation software (BoneViewer), Company Report, Orthree Co. Ltd. (http://www.orthree.jp/pdf/case_bv.pdf)
Non-patent literature 2: Bone and joint surgery simulation software (BoneSimulator), Company Report, Orthree Co. Ltd. (http://www.orthree.jp/pdf/case_bs.pdf)

SUMMARY OF THE INVENTION

Technical Problem

However, the technique described in patent literature 1 controls the attachment position of a robot to a skull but cannot support determination of an appropriate disposition of a bone in a living body. In addition, the techniques of non-patent literatures 1 and 2 are used to simulate bone and joint surgery in advance, and are not intended to support determination of an appropriate disposition of a bone in a living body during actual surgery.

The present invention enables to provide a technique of solving the above-described problems.

Solution to Problem

One aspect of the present invention provides a surgical operation support system comprising:

a storage that stores 3D data of a target bone that undergoes a surgical operation and position data of a marker in association with each other;
an image capturer that captures the marker of the target bone; and
a display that changes display of the target bone in accordance with a change in a position of the captured marker using the data stored in the storage.

Another aspect of the present invention provides a surgical operation support apparatus comprising:
a storage that stores 3D data of a target bone that undergoes a surgical operation and position data of a marker in association with each other;
an image capturer that captures the marker of the target bone; and
a display that changes display of the target bone in accordance with a change in a position of the captured marker using the data stored in the storage.

Still other aspect of the present invention provides a surgical operation support method comprising:
storing 3D data of a target bone that undergoes a surgical operation and position data of a marker in a storage in association with each other;
capturing the marker of the target bone; and
changing display of the target bone in accordance with a change in a position of the captured marker using the data stored in the storage.

Yet another aspect of the present invention provides a surgical operation support program that causes a computer to execute a method comprising:
storing 3D data of a target bone that undergoes a surgical operation and position data of a marker in a storage in association with each other;
capturing the marker of the target bone; and
changing display of the target bone in accordance with a change in a position of the captured marker using the data stored in the storage.

Still yet another aspect of the present invention provides an information processing apparatus comprising:
a storage that stores 3D data of a target bone that undergoes a surgical operation and position data of a marker in association with each other;
a receiver that receives, from an image capturer, an image of the marker of the target bone captured by the image capturer; and
a display image generator that generates a display image of the target bone, which changes in accordance with a change in a position of the captured marker, using the data stored in the storage.

Advantageous Effects of Invention

According to the present invention, it is possible to support determination of an appropriate disposition of a bone in a living body during surgery.

BRIEF DESCRIPTION OF THE DRAWINGS

FIG. 1 is a block diagram showing the arrangement of a surgical operation support system according to the first embodiment of the present invention.

FIG. 3B is a block diagram showing the arrangement of a preoperative preparation data generation system according to the second embodiment of the present invention;

FIG. 5B is a screen transition diagram of the intraoperative image processing system according to the second embodiment of the present invention;

FIG. 6 is a flowchart showing the processing procedure of a surgical operation support system according to the second embodiment of the present invention;

FIG. 7 is a view showing surgical operation support instruments used in the surgical operation support system according to the second embodiment of the present invention;

FIG. 8 is a block diagram showing a functional arrangement of an information processing apparatus in the preoperative preparation data generation system according to the second embodiment of the present invention;

FIG. 10 is a view showing the arrangement of an STL DB according to the second embodiment of the present invention;

FIG. 11 is a view showing the arrangement of a 3D preoperative preparation image data DB according to the second embodiment of the present invention;

FIG. 12 is a view showing the arrangement of a reference bone image generation table according to the second embodiment of the present invention;

FIG. 14 is a block diagram showing the functional arrangement of a tablet computer in the intraoperative image processing system according to the second embodiment of the present invention;

FIG. 15 is a view showing the arrangement of a marker DB according to the second embodiment of the present invention;

FIG. 16A is a view showing the arrangement of a marker analysis table according to the second embodiment of the present invention;

FIG. 16B is a view showing the arrangements of intraoperative target bone alignment tables according to the second embodiment of the present invention;

FIG. 24 is a block diagram showing the functional arrangement of an information processing apparatus in a preoperative preparation data generation system according to the fifth embodiment of the present invention;

FIG. 25 is a view showing the arrangement of a preoperative preparation data DB according to the fifth embodiment of the present invention;

FIG. 27 is a block diagram showing the functional arrangement of a tablet computer in an intraoperative image processing system according to the fifth embodiment of the present invention;

FIG. 29 is a block diagram showing the functional arrangement of an information processing apparatus in an intraoperative image processing system according to the sixth embodiment of the present invention;

FIG. 30 is a view showing a data table used by a bone image collator according to the sixth embodiment of the present invention; and FIG. 31 is a flowchart showing the processing procedure of the information processing apparatus in the intraoperative image processing system according to the sixth embodiment of the present invention.

DESCRIPTION OF THE EMBODIMENTS

Figure 2:
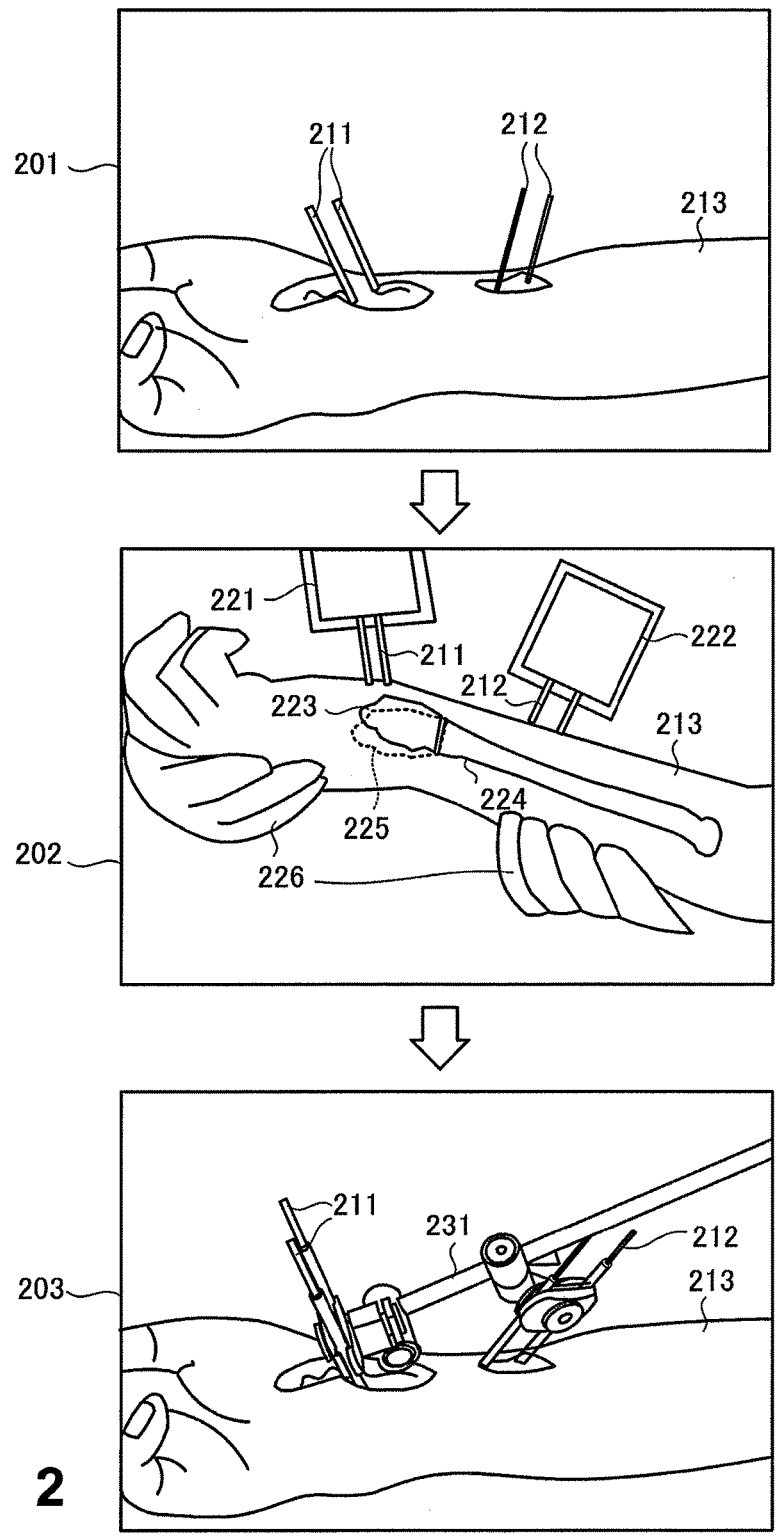
FIG. 2 is a view for explaining the outline of surgical operation support processing according to the second embodiment of the present invention.

Preferred embodiments of the present invention will now be described in detail with reference to the drawings. It should be noted that the relative arrangement of the components, the numerical expressions and numerical values set forth in these embodiments do not limit the scope of the present invention unless it is specifically stated otherwise.

First Embodiment

A surgical operation support system 100 according to the first embodiment of the present invention will be described with reference to FIG. 1. The surgical operation support system 100 is a system that supports a surgical operation by image processing.

As shown in FIG. 1, the surgical operation support system 100 includes a storage 110, an image capturer 120, and a display 150.

The storage 110 stores 3D data of a first target bone 111 that is one of two divided parts of a surgery target bone 101 and 3D data of a reference bone 113 partially overlapping the first target bone 111 in association with the position data of a first marker 102 fixed to the first target bone 111. The storage 110 also stores 3D data of a second target bone 112 that is the other of the two divided parts of the surgery target bone 101 in association with the position data of a second marker 103 fixed to the second target bone 112.

The image capturer 120 captures the first marker 102 fixed to the first target bone 111 and the second marker 103 fixed to the second target bone 112. The display 150 changes display in accordance with a change in the relative positions of the first marker 102 and the second marker 103 using the data stored in the storage 110 such that the target position of the second marker 103 with respect to the first marker 102 when the second target bone 112 overlaps the reference bone 113 can be grasped.

According to this embodiment, it is possible to support determination of an appropriate disposition of a bone in a living body during surgery.

Second Embodiment

A surgical operation support system according to the second embodiment of the present invention will be described next. The surgical operation support system according to this embodiment generates 3D data of a first target bone that is a part of a surgery target bone serving as the reference of the disposition of the surgery target bone and 3D data of a reference bone in advance, and stores the data in association with a first marker (for example, a 2D code) fixed to the first target bone. The surgical operation support system also generates 3D data of a second target bone that is the other part of the surgery target bone, and stores the data in association with a second marker (for example, a 2D code) fixed to the second target bone. In surgery, the 3D positions of the first target bone and the second target bone are determined from the captured first and second markers using the AR (Augmented reality) technology and displayed based on the stored 3D data. It is determined whether the second target bone and the reference bone adequately overlap, thereby determining an appropriate disposition of the surgery target bone. This processing supports determining an appropriate disposition of the surgery target bone by a doctor.

Surgical Operation Support System

The outline of the arrangement and processing of the surgical operation support system according to this embodiment will be described below with reference to FIGS. 2 to 7. The surgical operation support system is roughly divided into a preoperative preparation data generation system and an intraoperative image processing system. The preoperative preparation data generation system is a system that generates and displays 3D data of a first target bone, a second target bone, and a reference bone before surgery, and generates and stores data to be used during surgery. The intraoperative image processing system is a system that generates and displays a target bone image and a reference bone image based on marker image capturing, and supports determination of the disposition of the surgery target bone. However, the preoperative preparation data generation system and the intraoperative image processing system may be formed as one integrated system.

Outline of Surgical Operation

FIG. 2 is a view for explaining the outline of a whole surgical operation according to this embodiment. FIG. 2 shows an example of corrective osteotomy of an affected bone (surgery target bone) with malunion. The corrective osteotomy includes a preparation stage 201, a surgery target bone alignment stage 202, and a surgery target bone position fixing stage 203. In this embodiment, malunion surgery of a distal radius will be described as an example. However, the present invention is not limited to this, and is also applicable to malunion of another part or another bone or fracture treatment surgery.

In the preparation stage 201, pairs of pins 211 and 212 each having a predetermined interval (for example, an interval of 1 cm or 2 cm) are fixed as support members for two markers at two points sandwiching the bone cutting plane of the surgery target bone of a forearm 213. Portions having a sufficient strength and sectional area and capable of fixing two pins in the longitudinal direction of the surgery target bone are preferable as positions to insert and fix the pins. A length of about 5 cm to 10 cm suffices as a pin length that enables to set markers outside the forearm and easily capture them, although the length changed depending on the affected portion or bone. CT (Computed Tomography) imaging is performed in a state in which the pins 211 and 212 are fixed, thereby generating and storing 3D data of the surgery target bone. In addition, the positions and directions of markers to be fixed to the pins 211 and 212 later are set in advance to generate the position data of the markers. The position data of the markers, the 3D data of the surgery target bone, and the 3D data of the reference bone are associated with each other.

For example, the 3D data of pins included in the 3D data of the surgery target bone may be displayed, and the user may be caused to designate the proximal and distal end positions of the two pins using a pointing device or the like to define the position and direction of the marker to be attached to the pins. The relationship between a plane formed by the two pins and the position and direction of the marker may be set in advance or selected from a plurality of relationships (for example, the marker is parallel or perpendicular to the plane formed by the two pins, or makes an angle of 45° with respect to the plane). Alternatively, for example, 3D model data of the pins and 3D model data of one or a plurality of jigs to be used to fix the marker to the pins may be prepared. Then, the 3D model data may be overlaid in a 3D space on the 3D data of the pins acquired by CT imaging, and the jigs may be attached to define the position of the marker. The relationship between the position and direction of the marker and the positions and directions of the surgery target bone and the reference bone is thus stored in a database.

During surgery, the affected part is cut open, and bone cutting is carried out. After that, in the surgery target bone alignment stage 202, markers 221 and 222 are shot using a digital camera. The positions, sizes, and directions of the markers 221 and 222 are recognized from the captured image, and a database is referred to, thereby deriving the positions, sizes, and directions of surgery target bones. Surgery target bones 223 and 224 of the derived positions, sizes, and directions are displayed.

When the doctor holds the forearm 213 of the patient by a hand 226 and bends or twists the arm, the state of the marker 221 in the captured image changes. The surgery target bone 223 in the displayed image is displayed such that its display position, size, and tilt change in accordance with the change in the position, size, and tilt of the marker 221. On the other hand, 3D shape data of a reference bone 225 is stored in advance together with the relative relationship to the position, size, and tilt of the marker 222. When the marker 222 is captured, the reference bone 225 is displayed at a predetermined position. When the doctor finds a position at which the surgery target bone 223 overlaps the reference bone 225, the process advances to the surgery target bone position fixing stage 203.

In the surgery target bone position fixing stage 203, to maintain the determined appropriate relative disposition of the surgery target bones 223 and 224 in the forearm 213 of the patient, the pins 211 and 212 at the position at which the surgery target bone 223 overlaps the reference bone 225 are fixed by a fixing tool 231.

With the support by the surgical operation support system, it is possible to make the incision part small and speed up the surgery. Note that in FIG. 2, the pins 211 and 212 project outside the wound. However, the present invention is not limited to this. For example, pins that are short (1 to 2 cm) enough to put their distal ends within the wound may be used. During surgery (alignment stage 202), long pins may newly be connected to the short pins, and the markers 221 and 222 may then be attached.

Alternatively, only a bone may be captured by CT imaging without inserting pins, and virtual pins may be inserted into the thus generated CG data of the bone. After that, a wound may be opened during surgery, and actual pins may be inserted to the position as in the CG data. At this time, the position of a marker may be determined using the CG data of the bone with the virtual pins. A pattern (pattern with pins) that exactly fits on the bone of the affected part may be formed by a 3D printer, and pins may be inserted based on the pattern, thereby inserting actual pins to the same position as in the CG data. The marker may be attached to the pattern itself in a state in which the pattern is exactly fitted on the bone. Feature points of the bone captured by the digital camera may be discriminated and overlaid on the CG data with pins, thereby inserting the pins to the same position in the same direction as in the CG data. This can suppress the burden on the patient and establishment of an infectious disease after CT imaging with the pins being inserted.

Pin Fixing Processing

Figure 3A:
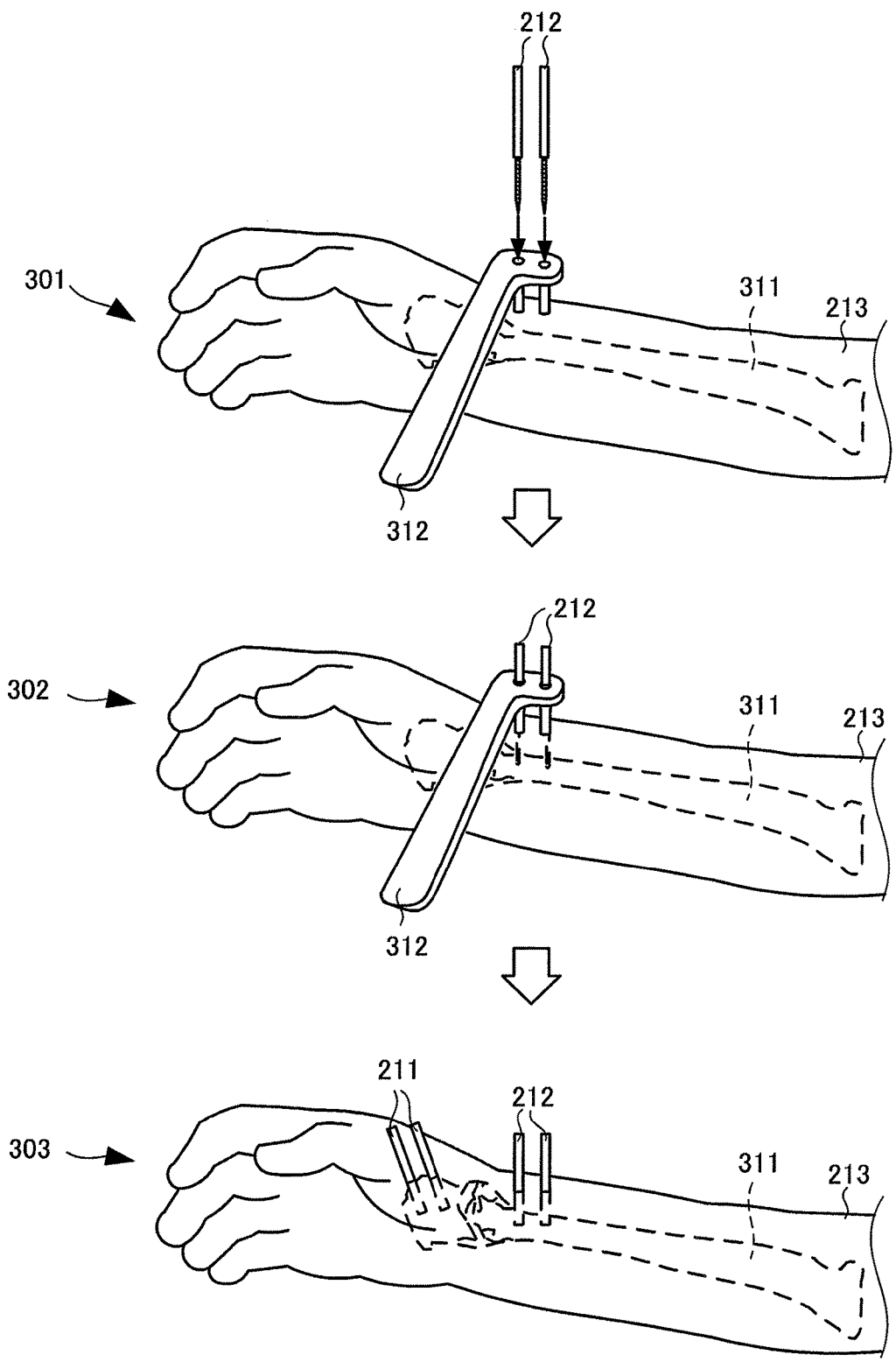
FIG. 3A is a view for explaining the outline of marker pin setting processing according to the second embodiment of the present invention.

FIG. 3A is a view for explaining the outline of insertion processing of marker pins (to be referred to as pins hereinafter) into a bone. FIG. 3A shows an example in which the pairs of pins 211 and 212 are fixed on two points of a surgery target bone 311 which sandwich an area estimated to include a bone cutting plane. FIG. 3A shows an alignment stage 301 of placing a pin fixing tube body 312 on the skin, a pin fixing stage 302 of inserting the pins into the pin fixing tube body 312 and fixing them to the bone, and a tube body removing stage 303.

First, in the alignment stage 301, the pin fixing tube body 312 is placed on the two points of the forearm 213 of the affected part which sandwich the area estimated to include a bone cutting plane. The pin fixing tube body 312 includes two tubular portions used to insert and fix the pins accurately at a predetermined interval. The pins 212 are inserted into the pin fixing tube body 312.

Next, in the pin fixing stage 302, the pins 212 inserted in the tubular portions are inserted into the forearm 213 of the affected part and fixed to the surgery target bone 311. Threads are cut on the distal ends of the pins 212. The pins are rotatably inserted into the bone.

In the tube body removing stage 303, only the pin fixing tube body 312 is removed while leaving the pins 212. The alignment stage 301, the pin fixing stage 302, and the tube body removing stage 303 as described above are repeated to fix the other pair of pins 211. The pins 211 and 212 are thus fixed to the surgery target bone 311.

Arrangement of Preoperative Preparation Data Generation System

FIG. 3B is a block diagram showing the arrangement of a preoperative preparation data generation system 320.

The preoperative preparation data generation system 320 includes an information processing apparatus 324 configured to generate a reference image, and a CT scanner 321 that acquires a tomographic image of a patient 322, which are connected via a network 323. The preoperative preparation data generation system 320 may also include, as an option, an STL data generation server 325 that generates 3D bone surface data (STL data) from tomographic image data. Note that the network can be either a WAN or a LAN.

In this embodiment, tomographic images of the affected part of the patient 322 and a part serving as the reference of the affected part are acquired by the CT scanner 321. In this example, for example, tomographic images of the right forearm in which four pins are inserted and fixed in the surgery target bone and tomographic images of the left forearm on the unaffected side are acquired. The tomographic image data are sent to the information processing apparatus 324 via the network 323 and converted into 3D data by the information processing apparatus 324. Note that the conversion from tomographic image data to 3D data may be done by the STL data generation server 325.

Note that living body data used in this embodiment is not limited to data acquired by CT/MRI, and 3D data is not limited to STL data.

Preoperative Preparation Data Generation Processing

Figure 4:
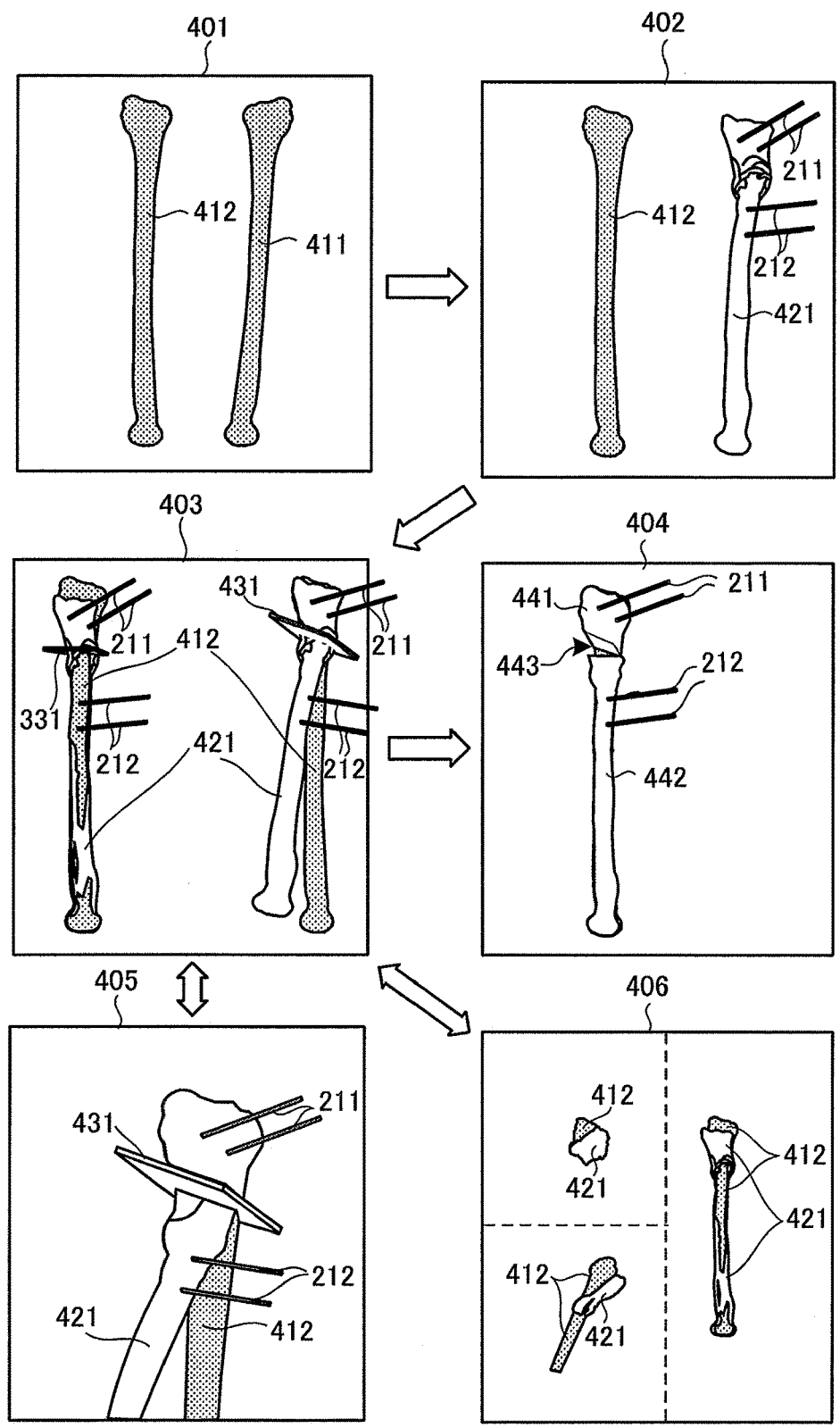
FIG. 4 is a view for explaining the outline of preoperative preparation image generation processing including reference bone image generation processing according to the second embodiment of the present invention.

FIG. 4 is a view for explaining the outline of preoperative preparation image generation processing using the information processing apparatus 324. Images 401 to 406 are CG (Computer Graphics) images displayed on the display screen of the information processing apparatus 324, which correspond to the stages of the preoperative preparation data generation processing, respectively.

In the first stage, as indicated by the image 401, an unaffected bone at a position (on the unaffected side) bilaterally symmetrical to the surgery target bone of the forearm 213 is internally captured by CT scan or the like. Thus generated 3D data 411 of the unaffected bone is inverted to generate mirror image data. Accordingly, 3D data (to be referred to as a reference bone hereinafter) 412 of a reference bone having the same shape as (at least partially overlapping) the surgery target bone is generated.

In the second stage, as indicated by the image 402, the surgery target bone of the forearm 213 is internally captured by CT scan or the like, and thus generated 3D data (to be referred to as a surgery target bone hereinafter) 421 of the surgery target bone (affected bone) is displayed. The surgery target bone 421 is generated from STL data captured in a state in which the pins 211 and 212 are fixed, and therefore includes the pins 211 and 212 even in the 3D data. The reference bone 412 and the surgery target bone 421 are compared on the display screen, and the state of the surgery target bone 421 is confirmed.

In the third stage, the surgery target bone 421 is manipulated on the image 403 while referring to the enlarged display image 405 in which the observation point in the 3D space is moved close to the surgery target bone or the divided display image 406 in which a plurality of images from different observation points (in this example, images from three directions) are simultaneously displayed. That is, the surgery target bone 421 is moved and rotated with respect to the reference bone 412 to overlay the end portions of the reference bone 412 on the end portions of the surgery target bone 421.

If the bone cutting plane can be estimated to exist on the upper end side, first, the lower ends of the surgery target bone 421 and the reference bone 412 are overlaid to determine the bone cutting plane of the surgery target bone 421, as shown on the left side. In particular, the shapes of the joint portions are overlaid to recognize the distortion, bending, or deformation of the surgery target bone 421. Then, the image is observed gradually from the lower end, and a branch position where deviation from the reference bone starts is determined as a bone cutting plane 431. Note that the doctor may determine the bone cutting plane 431 while observing the overlay state between the reference bone 412 and the surgery target bone 421. However, for example, a position where the non-overlay volume per unit length from the lower end between the surgery target bone 421 and the reference bone 412 exceeds a predetermined value may automatically be discriminated as the bone cutting plane 431. Alternatively, the surface of the reference bone 412 may finely be divided into unit areas, and positions at which the vertical distance to the surface of the surgery target bone 421 in each unit area exceeds a predetermined value may be connected to automatically derive the bone cutting plane 431.

The upper ends of the surgery target bone 421 and the reference bone 412 are overlaid, and the position of the section in the upper separated bone is confirmed, as shown on the right side of the image 403. When the bone cutting plane 431 is finally determined, the surgery target bone 421 is divided on the bone cutting plane 431, and 3D data of two target bones 441 and 442 are generated.

In the fourth stage, the set of the target bone 442 and the reference bone 412 which are overlaid is stored in association with the marker 222 attached to the pins 212. As indicated by the image 404, the target position of the target bone 441 with respect to the target bone 442 or the reference bone 412 is stored in association with the position data of the marker 221 attached to the pins 211. Accordingly, if the position or tilt of the marker 221 can be recognized in the real space, the target position or tilt of the target bone 441 can be estimated. Furthermore, the data of the position, shape, and tilt of the bone cutting plane 431 are stored in association with the position data of the marker 221 or 222. The position and direction of the marker 221 with respect to the pins 211 and the position and direction of the marker with respect to the pins 212 may be determined to one pattern in advance. In this embodiment, the position and direction can be selected from a plurality of (for example, four) patterns. In a first marker attachment type, a marker is attached to be parallel to the pin plane formed by the two pins. In a second marker attachment type, a marker is attached to a plane that is parallel to the axial direction of the pins and perpendicular to the pin plane. In a third marker attachment type, a marker is attached to a plane that is parallel to the axial direction of the pins and makes an angle of 45° with respect to the pin plane. In a fourth marker attachment type, a marker is attached to a plane that is parallel to the axial direction of the pins and makes an angle of 135° with respect to the pin plane. Alternatively, a marker may be attached to a plane perpendicular to the axial direction of the pins. The relative positional relationship between a marker and a surgery target bone or reference bone to be displayed is changed in accordance with how the marker is attached to the actual pins.

By using the thus prepared data, image display of the target bone 441 and the reference bone 412, image display of the target bone 442, and image display of the bone cutting plane 431 can be performed based on the positions, sizes, and directions of the markers captured in surgery. Note that a gap 443 between the target bone 441 and the target bone 442 represents the shape of a connecting bone necessary in surgery. Hence, the 3D shape of the connecting bone necessary in surgery can also be acquired at this time.

Note that in surgery, the combination of the target bones 441 and 442 determined as the target disposition on the image 404 may integrally be used and displayed without using the reference bone 412 generated from the unaffected side. In this case, the positions of the pins 211 and 212 serving as the support members of the first and second markers 221 and 223 in a state in which both of the target bones 441 and 442 are overlaid on the reference bone 412 are stored in the storage as target relative position data. The target positions of the pins 212 of the second marker 222 are displayed based on the stored target relative position data. In this embodiment, since corrective osteotomy of an affected bone (surgery target bone) with malunion is carried out, the bone cutting position is determined in this stage. In simple fracture treatment surgery, the bone cutting position need not be determined because a bone is separated into two from the beginning. That is, 3D data generated by CT scan or the like is directly used and overlaid on the reference bone. In the fourth stage, the rotation direction, the rotation angle, and the moving distance in millimeter with respect to the target bone 442 necessary for the target bone 441 to overlap the reference bone 412 may be stored as numerical values. This makes it possible to visually (by an image of an arrow or the like) indicate the rotation direction, the amount of rotation, the moving direction, and the amount of movement necessary for the marker 221 (that is, the arm) fixed to the actual pins 211 in surgery.

Arrangement of Intraoperative Image Processing System

Figure 5A:
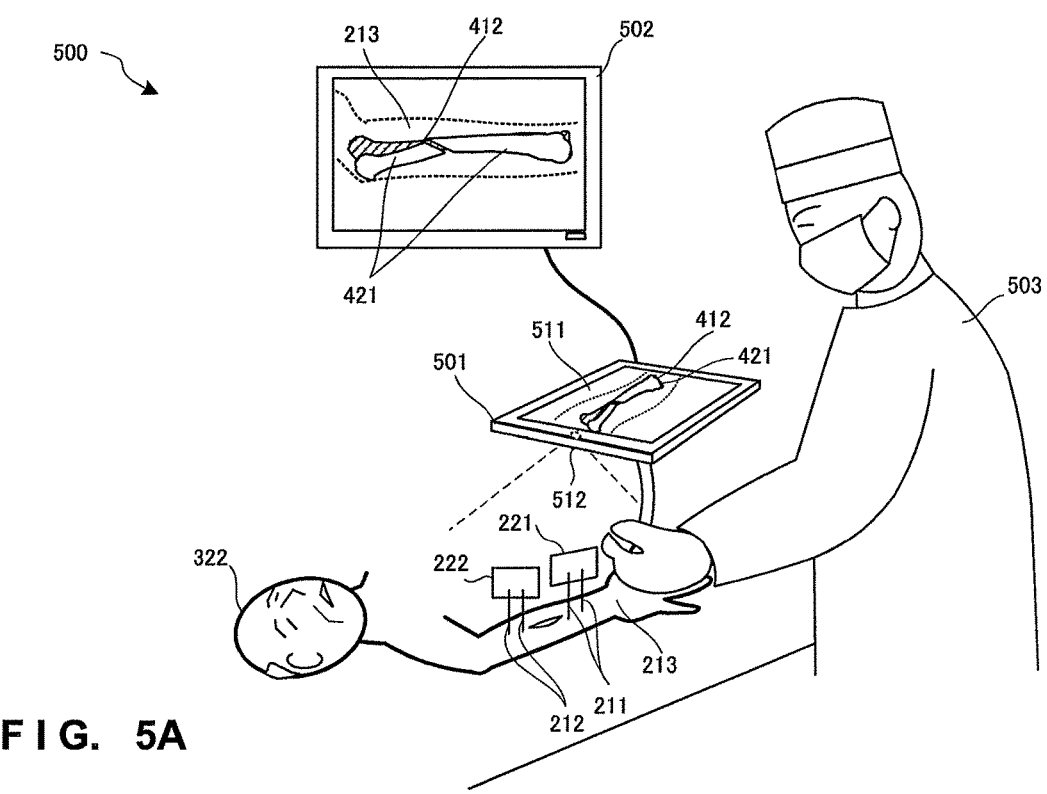
FIG. 5A is a view for explaining the outline of an intraoperative image processing system according to the second embodiment of the present invention.

FIG. 5A is a view showing the schematic arrangement of an intraoperative image processing system 500 according to this embodiment.

The intraoperative image processing system 500 includes a tablet computer 501 as an information processing apparatus, and a display device 502. The tablet computer 501 includes a display 511 and a camera 512.

The tablet computer 501 is fixed at a position at which the display 511 faces a doctor 503, and the camera 512 faces the markers 221 and 222. The tablet computer 501 stores the 3D data of the surgery target bone in advance, and recognizes the position and direction of the surgery target bone from the images of the markers 221 and 222. The tablet computer 501 displays the image of the surgery target bone at the recognized position on the display 511. Accordingly, the doctor 503 can grasp the positional relationship between the affected part and the bone in it at a glance.

When the doctor 503 holds the forearm 213 of the patient 322 and twists or stretches it, the positions of the markers 221 and 222 change accordingly. Hence, the surgery target bone 421 in the display 511 also moves or rotates. The forearm 213 is moved in this way to overlay the target bone 442 in the display 511 on the reference bone 412, thereby determining the target position of the surgery target bone. The pins 211 and 212 are fixed at the determined position using the fixing tool 231.

Intraoperative Target Bone Alignment Processing

FIG. 5B is a screen transition diagram for explaining the outline of a bone cutting operation and alignment operation of the surgery target bone during surgery. Before surgery, the markers 221 and 222 are fixed to the pins 211 and 212.

In a bone cutting stage, the bone cutting plane 431 is three-dimensionally displayed on the display 511, like an image 521, and the surgery target bone is cut at an appropriate position. In the image 521, a thick line indicates an image captured by the camera 512, and a thin line indicates a CG image generated from 3D data.

The doctor inserts a bone cutting blade into the affected part according to the bone cutting plane 431 and separate the affected bone with malunion. The doctor then manipulates the target bone 441 with respect to the target bone 442 by moving the forearm of the patient while referring to an image 522 of a coordinate space or divisionally displayed images 523 to 526. In the images 521 to 526, the target bones 441 and 442 of positions, sizes, and directions according to the positions, sizes, and directions of the markers 221 and 222 obtained by image capturing are displayed.

The image 522 displays the angles between the observation point and the X-axis, Y-axis, and Z-axis of the 3D space. The relative positions of the reference bone 412 and the target bones 441 and 442 in the 3D space are extracted and displayed. The image of the target bones 441 and 442 can be rotated on the screen by moving the observation point. The images 523 to 526 are divisionally displayed images displayed on one screen. The image 523 is the overlay image of the captured image and the CG image, like the image 521. The image 524 corresponds to only the CG image extracted from the image 523, and displays the reference bone and the target bone with the pins. The image 525 is the image of the reference bone 412 and the target bones 441 and 442 viewed from the axial direction of the bones, which makes an angle of 90° with respect to the camera 512. The image 526 is the image of the reference bone 412 and the target bones 441 and 442 viewed from the pin insertion direction which makes an angle of 90° with respect to the camera 512. That is, the images 524 to 526 are three display images with observation points in the three axial directions of the 3D space. The doctor determines an appropriate disposition of the target bones 441 and 442 while observing these display screens.

An image 527 shows a state in which the target bone 441 is overlaid on the reference bone 412. In this state, the pins 211 and 212 attached to the target bones 441 and 442 are fixed by the fixing tool.

Processing Procedure of Surgical Operation Support System

FIG. 6 is a flowchart showing the processing procedure of the entire surgical operation support system including the preoperative preparation data generation system 320 and the intraoperative image processing system 500.

First, in step S601, the preoperative preparation data generation system 320 acquires a tomographic image (for example, a CT image) of a surgery target bone to which pins are fixed and a tomographic image of an unaffected bone, and generates 3D data of the bones.

Next, in step S603, while displaying the generated 3D shape data, the bone cutting plane 431 and an appropriate disposition of the bone after bone cutting are determined, and the position data thereof are stored.

Then, in step S605, the intraoperative image processing system 500 captures markers fixed to the surgery target bone.

In step S607, the intraoperative image processing system 500 generates the bone image of the reference bone and the first target bone that changes in accordance with the movement of the marker and the bone image of the second target bone, and displays the bone images overlaid on the captured affected part image. The doctor moves the forearm while viewing the display screen.

In step S609, the intraoperative image processing system 500 confirms that the two target bones of the forearm are disposed such that the bone image of the second target bone matches the bone image of the reference bone. If the bone images do not match, the intraoperative image processing system 500 returns to step S605 to continue the processing until the target bones are disposed at the matching position.

Surgical Operation Support Instruments

FIG. 7 is a view showing surgical operation support instruments used in the surgical operation support system according to this embodiment. Note that instruments normally used in an inspection or surgery are not illustrated in FIG. 7.

The surgical operation support instruments include support instruments 710 used to fix the pairs of pins at two points of the surgery target bone before CT imaging of the surgery target bone or before the start of surgery after CT imaging of the surgery target bone. The surgical operation support instruments also include support instruments 720 used to attach a marker to two pins in surgery.

The support instruments 710 include the pairs of pins 211 and 212, the pin fixing tube body 312 used to insert the pins 211 and 212 exactly at an interval of 1 cm, and a pin fixing tube body 712 used to insert the pins 211 and 212 exactly at an interval of 2 cm.

The support instruments 710 are used as described with reference to FIG. 3A.

The support instruments 720 include 2D codes 721 each printed on paper or a plastic film, marker supports 722 to 725 that supports the 2D codes 729, pin connectors 727 and 728 used to attach the marker supports 722 to 725 to the pins, and an alignment jig 726 formed into an inverted L shape and used to align the connectors 727 and 728.

The marker support 722 is a support that attaches a marker in parallel to a pin plane formed by two pins. The marker support 723 is a support that attaches a marker to a plane that is parallel to the axial direction of the pins and perpendicular to the pin plane. The marker support 724 is a support that attaches a marker to a plane that is parallel to the axial direction of the pins and makes an angle of 45° (45° to the right) with respect to the pin plane. The marker support 725 is a support that attaches a marker to a plane that is parallel to the axial direction of the pins and makes an angle of 135° (45° to the left) with respect to the pin plane. The marker supports according to the present invention are not limited to these, and a support that attaches a marker to a plane perpendicular to the axial direction of the pins or a support with a hinge capable of attaching a marker in an arbitrary direction with respect to the pins may be prepared. The relative positional relationship between the marker and the surgery target bone or reference bone to be displayed is changed in accordance with the manner the marker is attached to the actual pins.

The alignment jig 726 includes a convex portion 726a, a concave portion 726b, and groove portions 726c. The convex portion 726a and the concave portion 726b are formed into sizes that exactly fit in or on concave portions 727b and 728b and convex portions 727a and 728a provided on the pin connectors 727 and 728.

First, in the first step, the alignment jig 726 and the pin connector 727 are combined using the concave portions and the convex portions. In the second step, the pins are inserted along the grooves 726c and 727c. The pin connector 727 and the pins are fixed by a screw 727d at a position where the pins abut against a ceiling surface 726d. In the third step, the alignment jig 726 is detached from the pin connector 727. The first to third steps are repeated in a similar manner, thereby connecting the pin connector 728 and the pins at an accurate position using the alignment jig 726.

The pins 211 and 212 are thus accurately connected to the pin connectors 727 and 728, respectively.

Each of the marker supports 722 to 725 also includes a convex portion and a concave portion. The convex portions 727a and 728a and the concave portions 727b and 728b are fitted, thereby fixing one of the marker supports 722 to 725 to one of the pin connectors 727 and 728.

Functional Arrangement of Information Processing Apparatus in Preoperative Preparation Data Generation System FIG. 8 is a block diagram showing a functional arrangement example 324A of the information processing apparatus 324. Note that FIG. 8 shows CT data as tomographic image data, and STL data as 3D bone surface model data. However, the data are not limited to these. Each functional unit of the information processing apparatus 324A is implemented when a CPU processes image data by executing a program using a memory.

A CT data acquirer 811 shown in FIG. 8 acquires CT data (DICOM) from the CT scanner 321 as an image of the patient 322. A CT database 812 searchably accumulates the CT data acquired by the CT data acquirer 811.

A bone shape data generator 813 generates STL data from the CT data as 3D bone surface model data. An STL data DB 814 searchably accumulates the STL data generated by the bone shape data generator 813.

A display/operation unit 815 is formed from a display, a touch panel, or the like. The display/operation unit 815 performs 3D display of a bone image based on the STL data generated by the bone shape data generator 813, and performs 3D movement (rotation and movement) of the bone image in accordance with an instruction of the doctor. In this example, the image of the surgery target bone and the image of the unaffected bone of the patient 322 are displayed simultaneously such that they can be overlaid. The display/operation unit 815 can also input bone cutting position information of the surgery target bone. The display/operation unit 815 can independently display 3D movement (rotation and movement) of a plurality of partial bones (first target bone/second target bone) obtained by cutting and separating the surgery target bone at the bone cutting position. A reference bone data generator 816 laterally inverts the 3D data of the unaffected bone, thereby generating reference bone data.

A 3D data generator 817 overlays the 3D shape data of the first target bone separated based on the bone cutting position information and that of the reference bone in a virtual 3D space to generate 3D standard bone data. The generated 3D standard bone data is stored in a preoperative preparation data DB 819. A 3D data generator 818 generates 3D shape data of the second target bone. The generated 3D shape data is stored in the preoperative preparation data DB 819. Overlay of the target bone and the reference bone may be done based on an operation of the doctor or automatically performed by the 3D data generators 817 and 818 based on the bone shape (in particular, the shape of a joint portion). The preoperative preparation data DB 819 accumulates the 3D data generated by the 3D data generators 817 and 818 such that the 3D data can be searched by STL data. The STL data accumulated in the preoperative preparation data DB 819 is used by the intraoperative image processing system 500.

Figure 9:
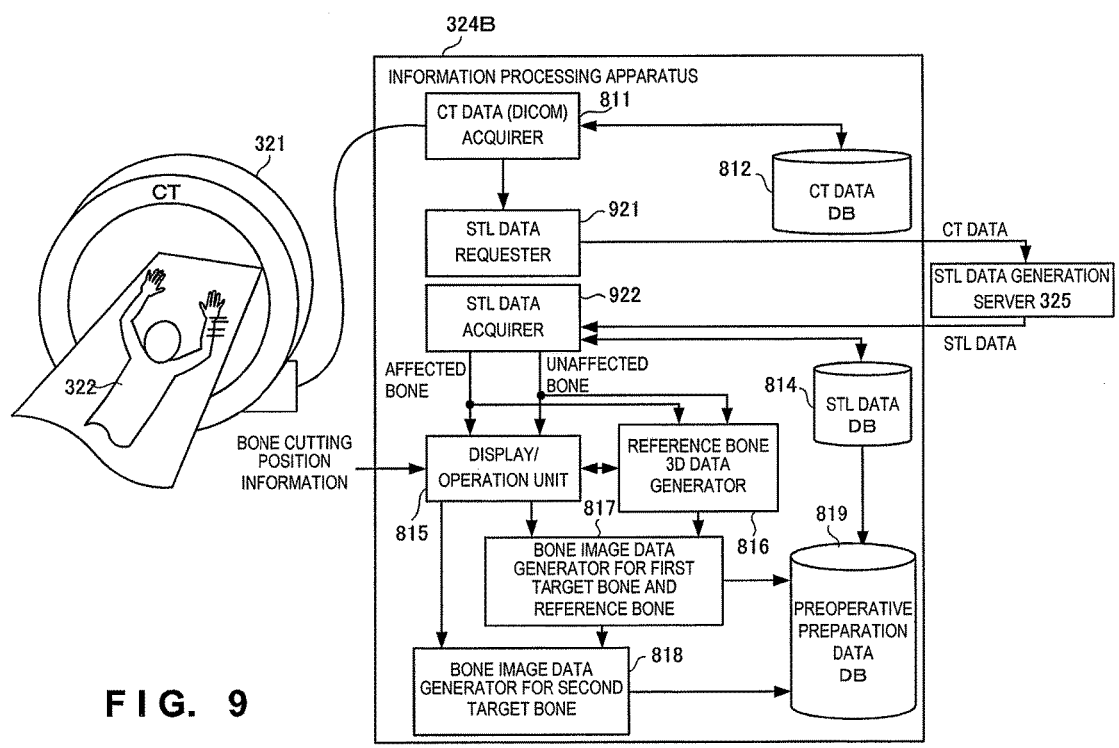
FIG. 9 is a block diagram showing another functional arrangement of the information processing apparatus in the preoperative preparation data generation system according to the second embodiment of the present invention.

FIG. 9 is a block diagram showing another functional arrangement example 324B of the information processing apparatus 324. Note that the same reference numerals as in FIG. 8 denote the same functional components in FIG. 9, and a description thereof will be omitted. Each functional unit shown in FIG. 9 is implemented when a CPU processes image data by executing a program using a memory.

In the arrangement shown in FIG. 9, the information processing apparatus 324 does not have the function of generating STL data from CT data (the program is not installed), unlike the arrangement shown in FIG. 8. Hence, STL data is requested from the external STL data generation server 325. An STL data requester 921 transmits CT data to the STL data generation server 325 and requests it to generate STL data. An STL data acquirer 922 receives generated STL data from the STL data generation server 325. Note that the CT data to the STL data generation server 325 or the STL data from the STL data generation server 325 may be transmitted/received using a storage medium.

STL Data DB

FIG. 10 is a view showing the arrangement of the STL data DB 814 according to this embodiment. The STL data DB 814 searchably accumulates STL data representing a 3D bone surface model according to this embodiment. Note that the arrangement of the STL data DB 814 is not limited to that shown in FIG. 10.

The STL data DB 814 stores a CT data acquisition date/time 1002, a patient name 1003, an affected part 1004, a symptom 1005, and CT data 1006 in association with an image ID 1001. The STL data DB 814 also stores STL data 1007 generated from the CT data 1006, and an STL data generation source 1008 if the STL data is externally generated.

3D Preoperative Preparation Image DB

FIG. 11 is a view showing the arrangement of the preoperative preparation data DB 819 according to this embodiment. The preoperative preparation data DB 819 searchably accumulates STL data representing a 3D bone image according to this embodiment. Note that the arrangement of the preoperative preparation data DB 819 is not limited to that shown in FIG. 11.

The preoperative preparation data DB 819 stores an affected part 1102, a symptom 1103, 3D data 1104 associated with a first marker, and 3D data 1105 associated with a second marker in association with a patient name 1101. The 3D data 1104 includes the 3D data of a first target bone, the 3D position data of a first marker support instrument, and the 3D data of a reference bone. The 3D data 1105 includes the 3D data of a second target bone and the 3D position data of a second marker support instrument. Note that the 3D data 1104 and 1105 are stored in a format that allows a displayed bone image to move and rotate in the 3D space.

Reference Bone Image Generation Table

FIG. 12 is a view showing the arrangement of a reference bone data generation table 1200 according to this embodiment. The reference bone data generation table 1200 is a table used by the reference bone data generator 816 shown in FIG. 8 or 9 to generate reference bone data.

The reference bone data generation table 1200 stores a patient name 1202, an affected part 1203, a symptom 1204, unaffected bone STL data 1205, and reference bone STL data 1206 as a reference bone in association with a 3D reference bone image ID 1201.

Processing Procedure of Information Processing Apparatus

Figure 13:
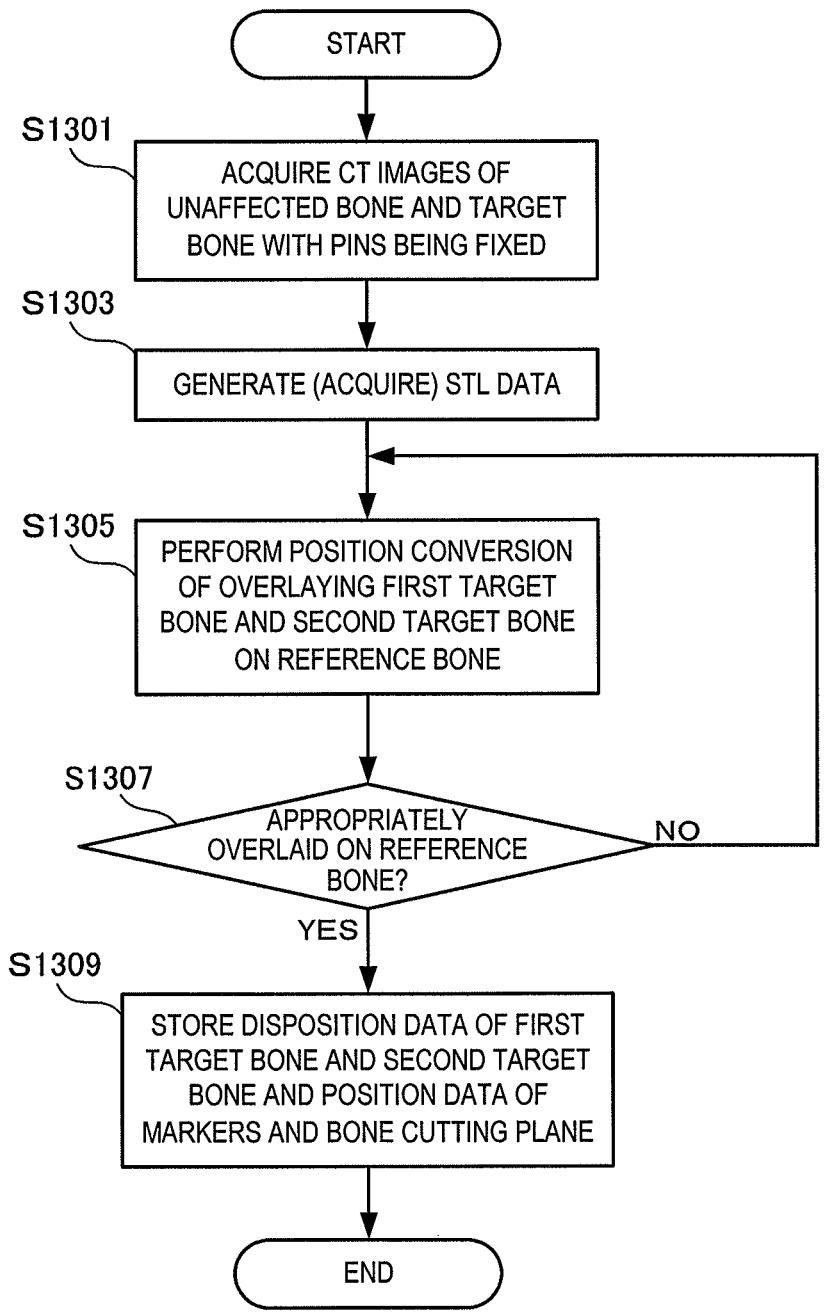
FIG. 13 is a flowchart showing the processing procedure of the information processing apparatus in the preoperative preparation data generation system according to the second embodiment of the present invention.

FIG. 13 is a flowchart showing a processing procedure in the information processing apparatus 324. This flowchart is executed by the CPU of the information processing apparatus 324 using a RAM as a preoperative preparation data generation program to implement the functional components shown in FIG. 8 or 9.

In step S1301, the information processing apparatus 324 acquires the CT images of an unaffected bone and a target bone with pins being fixed. In step S1303, the information processing apparatus 324 generates STL data from the CT image data. The information processing apparatus 324B shown in FIG. 9 transmits the CT image data and acquires STL data.

In step S1305, the information processing apparatus 324 performs position conversion (STL data coordinate conversion) of setting a bone cutting plane and overlaying a first target bone and a second target bone separated at the bone cutting plane on the reference bone. In step S1307, the information processing apparatus 324 determines whether the surgery target bone and the reference bone are appropriately overlaid. If the overlay is automatic processing of the information processing apparatus 324, the determination is done by shape determination.

If the target bone and the reference bone are not appropriately overlaid, the information processing apparatus 324 returns to step S1305 to repeat rotation and movement of the second target bone with respect to the first target bone. If the target bone and the reference bone are appropriately overlaid, in step S1309, the information processing apparatus 324 stores the 3D data of the target bone and the reference bone and the position data of the markers and the bone cutting plane with the positional relationship in the preoperative preparation data DB 819.

Functional Arrangement of Information Processing Apparatus in Intraoperative Image Processing System FIG. 14 is a block diagram showing the functional arrangement of the tablet computer 501 in the intraoperative image processing system 500 according to this embodiment. Each functional unit of the tablet computer 501 is implemented when a CPU (not shown) executes a program using a memory. Note that in this embodiment, the tablet computer 501 is used. However, the present invention is not limited to this, and any information processing terminal including a display and a camera is usable. The camera or display/operation unit may be separated from the information processing apparatus, and data communication may be performed between them.

The camera 512 captures an affected part of the patient 322 in an operating room. The image capturing range of the camera 512 includes the markers 221 and 222 fixed at two points of the surgery target bone of the forearm 213 of the patient 322. A marker analyzer 1411 refers to a marker DB 1412, and analyzes the type of an image to be displayed and the position and direction to display the image from a marker image captured by the camera 512.

Preoperative preparation data 1419 is the same as the data stored in the preoperative preparation data DB 819 shown in FIG. 8 or 9. For example, the preoperative preparation data 1419 may be duplicated from the information processing apparatus 324 shown in FIG. 8 or 9 to the tablet computer 501 by communication or copied via a storage medium. Alternatively, the preoperative preparation data 1419 may be acquired by accessing from the tablet computer 501 to the preoperative preparation data DB 819 in the information processing apparatus 324 directly by communication.

A CG image generator 1414 generates a CG image to be displayed, based on the 3D position and direction of each marker acquired from the marker analyzer 1411, the 3D data of the target bone and the reference bone included in the preoperative preparation data 1419, and the like. The CG image generator 1414 functions as a first bone image generator that generates the bone image of the first target bone and the bone image of the reference bone from the 3D data of the first target bone and the 3D data of the reference bone based on the position, size, and direction of the captured first marker. The CG image generator 1414 also functions as a second bone image generator that generates the bone image of the second target bone from the 3D data of the second target bone based on the position, size, and direction of the captured second marker.

A display image generator 1415 overlays the surgery target bone image and the reference bone image generated by the CG image generator 1414 on the affected part image of the forearm 213 of the patient 322 captured by the camera 512 to generate display image data for the display. The display 511 thus simultaneously displays the target bone image and the reference bone image overlaid on the affected part image. It is also possible to display an image from a moved observation point or simultaneously display images from a plurality of observation points. That is, to search for the positions of the first marker and the second marker at which the second target bone overlaps the reference bone, the display image generator 1415 displays the bone image of the first target bone, the bone image of the reference bone, and the bone image of the second target bone. In this display, the display image generator 1415 displays the bone image of the first target bone and the bone image of the second target bone such that their relative positions change in accordance with a change in the relative positions of the first marker and the second marker.

Marker DB

FIG. 15 is a view showing the arrangement of the marker DB 1412 according to this embodiment. The marker DB 1412 is used by the marker analyzer 1411 to analyze the 3D position and direction of each marker (that is, the position and direction of a pair of pins) from image data captured by the camera 512.

The marker DB 1412 stores matrix data 1502 in a case in which a 2D code is captured from the front side in association with a marker ID 1501. Here, the matrix data 1502 arranges, for example, binary or multilevel bit data representing white/black or colors on 2D coordinates. A 3D position and direction can be recognized based on a change in coordinate values. Note that the 2D code is not limited to this. The marker DB 1412 also stores a marker shape 1503 in a case in which the marker is captured from the front side, and a marker size 1504 at a predetermined distance.

Marker Analysis Table

FIG. 16A is a view showing the arrangement of a marker analysis table 1601 used by the marker analyzer 1411. The marker analysis table 1601 is a table used to obtain 2D data on the marker, the position, size, and direction of the marker, or 3D data of a marker support instrument from the image of a marker captured by the camera 512 and generate 3D display data of the target bone image or reference bone image.

The marker analysis table 1601 stores a 2D code frame 1611 of a marker extracted from a capture image, matrix data 1612 of the 2D code of the marker, and a marker ID 1613 discriminated from the matrix data 1612. The marker analysis table 1601 also stores a position, size, and direction 1614 of the marker, and a 3D position and direction 1615 of the marker calculated from the position, size, and direction 1614 of the marker. The position, size, and direction to display 3D data of the target bone to be displayed on the display can be determined in accordance with the 3D position and direction 1615 of the marker.

3D Data Generation Table

FIG. 16B is a view showing the arrangement of intraoperative target bone alignment tables 1602 and 1603 used by the CG image generator 1414. The intraoperative target bone alignment table 1602 stores analyzed 3D position data 1622 of the first marker, and 3D position data 1623 of the first marker stored in the preoperative preparation data DB 819 in association with a first target bone and reference bone ID 1621. Using a conversion vector that converts the 3D position data 1623 of the first marker into the 3D position data 1622, the coordinates of 3D data of the first target bone stored in the preoperative preparation data DB 819 are converted. The intraoperative target bone alignment table 1602 stores 3D data 1624 of the first target bone for display, which is generated by the coordinate conversion. In addition, the coordinates of the 3D data of the reference bone stored in the preoperative preparation data DB 819 are converted using the same conversion vector, thereby generating and storing 3D data 1625 of the reference bone for display.

The intraoperative target bone alignment table 1603 stores analyzed 3D position data 1632 of the second marker, and 3D position data 1633 of the second marker stored in the preoperative preparation data DB 819 in association with a second target bone ID 1631. Using a conversion vector that converts the 3D position data 1633 of the second marker into the 3D position data 1632, the coordinates of 3D data of the second target bone stored in the preoperative preparation data DB 819 are converted. The intraoperative target bone alignment table 1603 stores 3D data 1634 of the second target bone for display, which is generated by the coordinate conversion.

Figure 17:
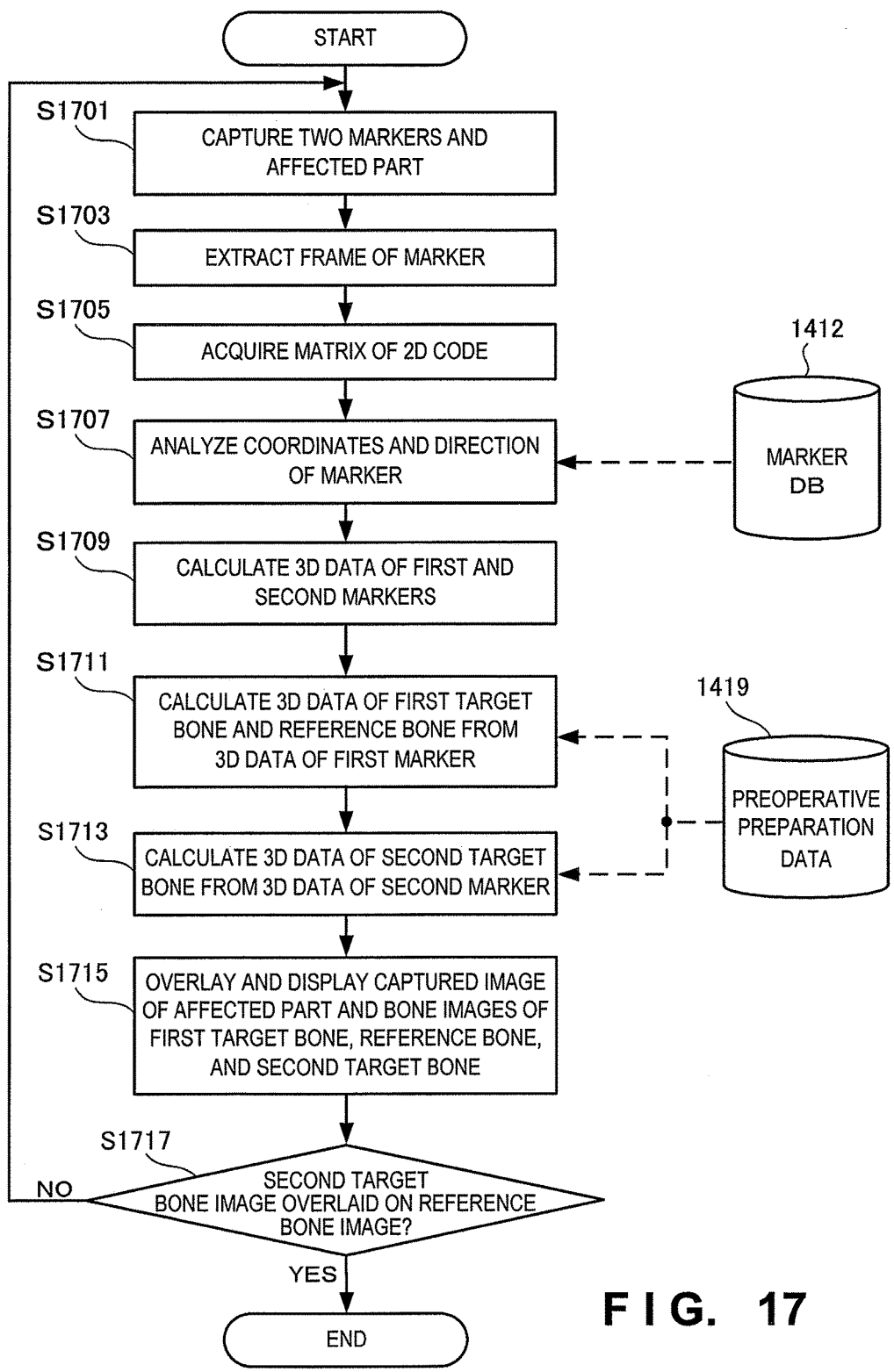
FIG. 17 is a flowchart showing the processing procedure of the tablet computer in the intraoperative image processing system according to the second embodiment of the present invention.

Processing Procedure of Information Processing Apparatus in Intraoperative Image Processing System FIG. 17 is a flowchart showing the processing procedure of the tablet computer 501 according to this embodiment. This flowchart is executed by the CPU of the tablet computer 501 using a RAM as an intraoperative image generation program to implement the functional components shown in FIG. 14.

In step S1701, the tablet computer 501 captures an affected area (in this example, the forearm portion) and acquires image data of two markers and the affected part image. In step S1703, the tablet computer 501 extracts a frame including a 2D code from the image data of the affected area. Note that in this example, the frame including the 2D code has a rectangular shape. However, a circular shape or any other shape is also usable. In step S1705, the tablet computer 501 acquires the matrix of the 2D code in the frame.

In step S1707, the tablet computer 501 compares the acquired matrix of the 2D code and the 2D code viewed from the front side, which is stored in the marker DB 1412, thereby specifying the marker. The tablet computer 501 also analyzes the marker coordinate system (the position and direction in the 3D space) in consideration of the position, size, and direction of the marker. In step S1709, the tablet computer 501 calculates the 3D data of the first marker fixed to the first target bone and the 3D data of the second marker fixed to the second target bone based on the analyzed 3D positions and directions of the markers. In step S1711, the tablet computer 501 calculates the 3D data of the first target bone and the reference bone for display from the calculated 3D data of the first marker support instrument based on 3D data stored as the preoperative preparation data 1419. In step S1713, the tablet computer 501 calculates the 3D data of the second target bone for display from the calculated 3D data of the second marker support instrument based on 3D data stored in the preoperative preparation data DB 819. In step S1715, the tablet computer 501 overlays and displays the captured affected part image, the generated images of the first target bone and the reference bone, and the generated bone image of the second target bone.

In step S1717, the tablet computer 501 determines whether the generated second target bone image is appropriately overlaid on the reference bone image. If the reference bone image and the generated second target bone image are not appropriately overlaid, the tablet computer 501 returns to step S1701 to detect the positions and directions of the two markers according to the movement of the surgery target bone again. If the reference bone image and the generated second target bone image are appropriately overlaid, the processing ends. Note that in actuality, the pins at two points are fixed when the reference bone image and the generated second target bone image are appropriately overlaid, thereby fixing the disposition of the surgery target bone at an appropriate position.

According to this embodiment, since an appropriate disposition of the surgery target bone can be determined without making a large incision in the affected part, surgery can be performed with a minimum incision in the affected part. In addition, since the appropriate disposition of the surgery target bone is determined by preoperative processing, surgery can be carried out quickly and properly. That is, it is possible to support an accurate disposition of the surgery target bone, accurate setting of the bone cutting position, creation of a necessary connecting bone, and proper bone-setting processing at the time of surgery.

Note that in this embodiment, the bone cutting plane 431 is determined in advance by the method described with reference to FIG. 4, and the determined bone cutting plane 431 is also presented to the doctor during surgery to attain accuracy in bone cutting. However, the present invention is not limited to this. For example, concerning bone cutting, the plane may be determined during surgery. In this case, the AR technology may be used to only accurately set the relative positional relationship between the two bones sandwiching the bone cutting plane to the reference bone. In this case, the pins need not be inserted before surgery, as shown in FIG. 3B. That is, after the bone cutting plane is set at an appropriate position, only the relative moving distances and rotation angles of the separated target bones 441 and 442 to attain a disposition at an ideal position, as indicated by the image 404 shown in FIG. 4, are stored. This obviates the necessity of performing CT scan of the bone with the pins inserted in advance. The pins are inserted at appropriate positions sandwiching the bone cutting plane, and the markers are attached during surgery. Since how the relative positional relationship of the pins before bone cutting needs to be changed after bone cutting is known, the target displacement (rotation amount, rotation direction, moving amount, and moving direction) of the bone is displayed using an arrow or the like and presented to the doctor. Especially in normal fracture treatment, since a bone is separated into two from the beginning, the bone cutting position need not be determined. That is, 3D data generated by CT scan or the like is directly used and overlaid on the reference bone.

In the fourth stage, the rotation direction, the rotation angle, and the moving distance in millimeter with respect to the target bone 442 necessary for the target bone 441 to overlap the reference bone 412 may be stored as numerical values. This makes it possible to visually (by an image of an arrow or the like) indicate the rotation direction, the amount of rotation, the moving direction, and the amount of movement necessary for the marker 221 (that is, the arm) fixed to the actual pins 211 in surgery.

Third Embodiment

A surgical operation support system according to the third embodiment of the present invention will be described next. The surgical operation support system according to this embodiment is different from the second embodiment in that an affected part and a display screen can be overlaid and observed using a head mounted display (Eye-Trek). The rest of the components and operations is the same as in the second embodiment. Hence, the same reference numerals denote the same components and operations, and a detailed description thereof will be omitted. Note that in this embodiment, a binocular head mounted display 1801 includes a stereo camera and can therefore perform 3D image capturing. The binocular head mounted display 1801 is a binocular optical see-through type, and can perform 3D display. However, one camera may be provided to do 2D display. The head mounted display may be a monocular type or video see-through type.

Arrangement of Intraoperative Image Processing System

Figure 18:
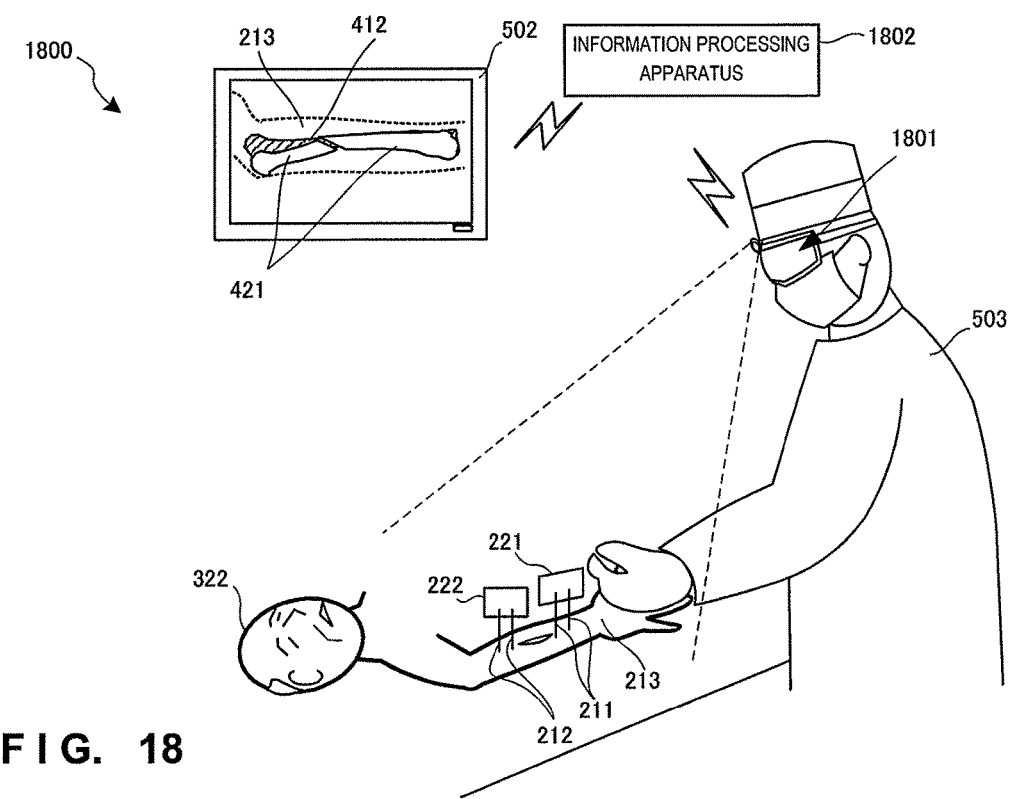
FIG. 18 is a view showing the arrangement of an intraoperative image processing system according to the third embodiment of the present invention.

FIG. 18 is a view showing the schematic arrangement of an intraoperative image processing system 1800 according to this embodiment. Note that the same reference numerals as in FIG. 5A denote the same constituent elements in FIG. 18, and a description thereof will be omitted.

The binocular head mounted display 1801 serves as glasses also functioning as a display with a camera. With the binocular head mounted display 1801, markers 221 and 222 in an affected area (in this example, the forearm portion) of a patient 322 can be captured by the camera, and a target bone image and a reference bone image can be displayed. In addition, the affected part of the patient 322 can be seen through via the display.

When the binocular head mounted display 1801 is used, it is possible to overlay and observe the affected part of the patient and the display screen for alignment.

Processing of Information Processing Apparatus

Figure 19:
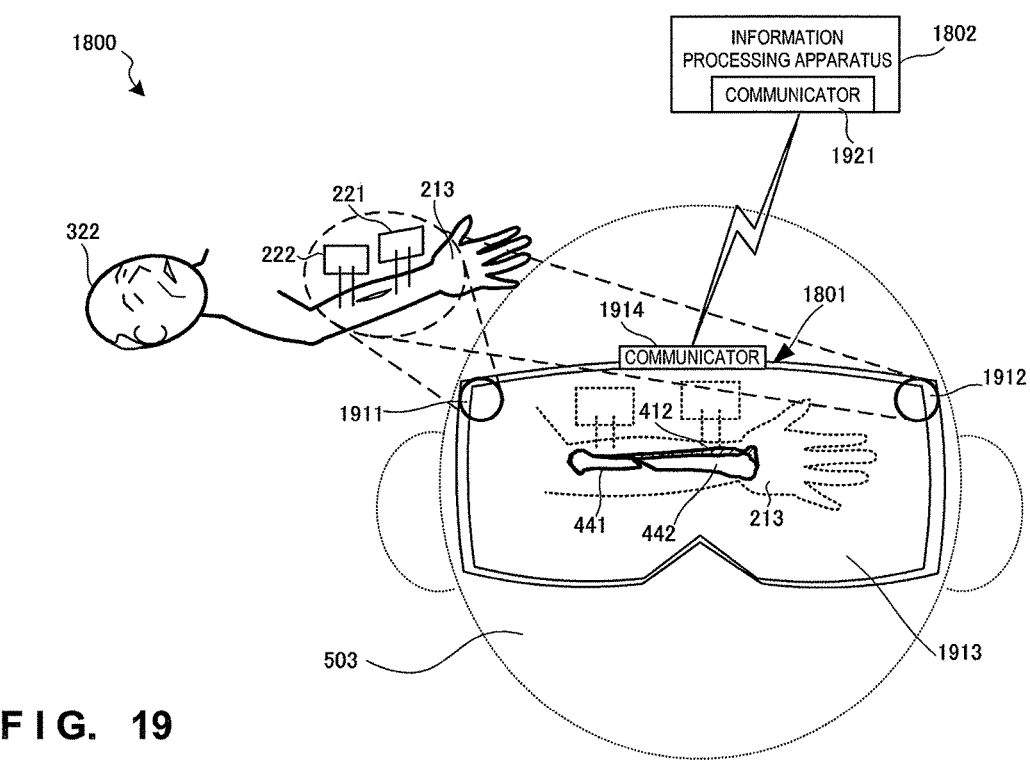
FIG. 19 is a view for explaining the processing of a tablet computer in the intraoperative image processing system according to the third embodiment of the present invention.

FIG. 19 is a view for explaining the processing of an information processing apparatus 1802 of the intraoperative image processing system 1800 according to this embodiment. Note that the same constituent elements as in FIG. 5A are not illustrated in FIG. 19, or a description thereof will be omitted. Alternatively, the constituent elements are denoted by the same reference numerals, and a description thereof will be omitted.

The binocular head mounted display 1801 includes cameras 1911 and 1912 that capture the markers 221 and 222, a display 1913 that displays a reference bone image and a target bone image, and a communicator 1914 that communicates with the information processing apparatus 1802. The display 1913 displays the CG images of target bones 441 and 442 and a reference bone 412. Since the display 1913 is a translucent display, a forearm 213 that is the affected part of the patient 322 can be observed through the display, as indicated by the broken line. Note that although FIG. 19 shows the two cameras 1911 and 1912, one camera may be used. A camera may separately be prepared.

Note that the information processing apparatus 1802 shown in FIG. 19 has an arrangement obtained by removing the camera 512 and the display 511 from the functional arrangement of the tablet computer 501 described with reference to FIG. 14 and providing a communicator 1921. Hence, the information processing apparatus 1802 receives the image data of the 2D codes of the markers 221 and 222 from the cameras 1911 and 1912, and transmits display data of a prepared reference bone image and a generated target bone image to the display 1913, unlike the tablet computer 501.

Figure 20:
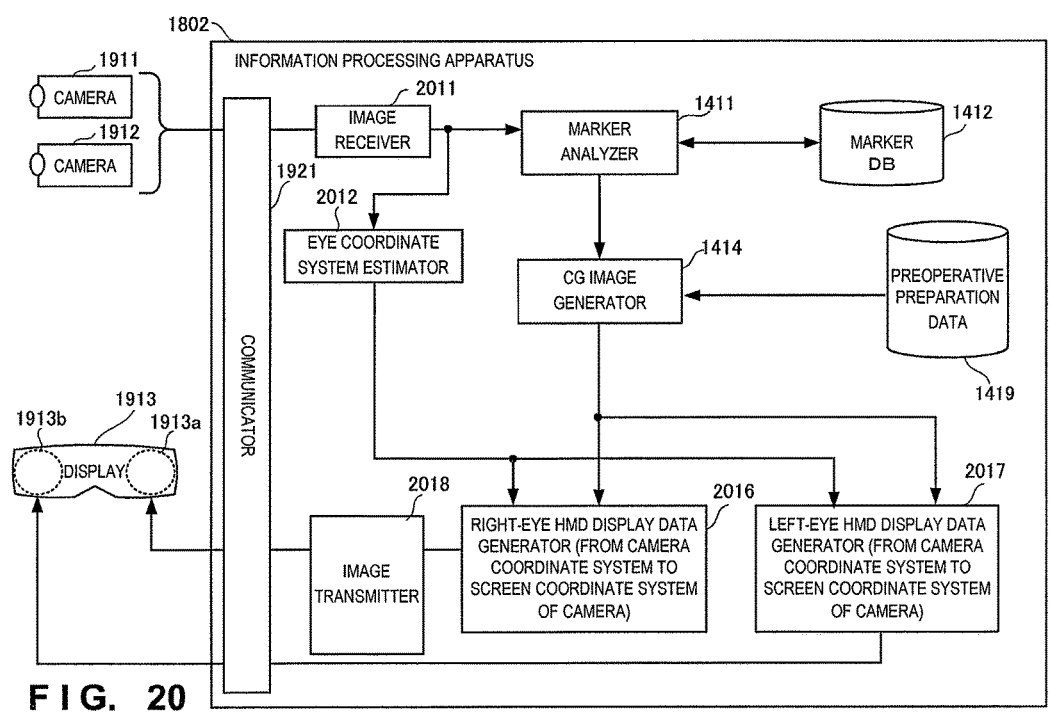
FIG. 20 is a block diagram showing the arrangement of the tablet computer in the intraoperative image processing system according to the third embodiment of the present invention.

Functional Arrangement of Information Processing Apparatus in Intraoperative Image Processing System FIG. 20 is a block diagram showing the arrangement of an information processing apparatus 2110 in the intraoperative image processing system according to this embodiment. Note that the same reference numerals as in FIG. 14 denote the same functional components in FIG. 20, and a description thereof will be omitted.

The communicator 1921 controls reception of image data from the cameras 1911 and 1912 and transmission of display image data to the display 1913 (a right-eye unit 1913a and a left-eye unit 1913b) of the binocular head mounted display 1801. An image receiver 2011 receives the image data of images captured by the cameras 1911 and 1912.

An eye coordinate system estimator 2012 estimates an eye coordinate system based on the line of sight or visual field of the doctor wearing the binocular head mounted display 1801 from the received captured image data of the cameras 1911 and 1912.

A right-eye HMD display data generator 2016 refers to eye coordinate system information from the eye coordinate system estimator 2012, and converts display image data on a 3D camera coordinate system into right-eye display data for a 2D HMD screen coordinate system. A left-eye HMD display data generator 2017 refers to the eye coordinate system information from the eye coordinate system estimator 2012, and converts display image data on the 3D camera coordinate system into left-eye display data for the 2D HMD screen coordinate system. The display position of the converted display data for the 2D HMD screen coordinate system is adjusted such that the 3D target bone image and the reference bone image overlap the forearm 213 of the affected part seen through the display 1913 of the binocular head mounted display 1801. It is also possible to display an image from a moved observation point or simultaneously display images from a plurality of observation points. Note that image display conversion by moving the observation point can be performed by converting the coordinate system, and a detailed description thereof will be omitted. An image transmitter 2018 transmits the display image data for the 2D HMD screen coordinate system to the display 1913 of the binocular head mounted display 1801 via the communicator 1921.

According to this embodiment, since the affected part of the patient and the display screen for alignment can be overlaid and observed, the burden on the doctor in alignment can be reduced. Note that considering the influence of wireless communication in the operating room, wired communication may be used between the glasses and the information processing apparatus.

Fourth Embodiment

A surgical operation support system according to the fourth embodiment of the present invention will be described next. The surgical operation support system according to this embodiment is different from the second embodiment and the third embodiment in that the degree of overlay (matching ratio) between a surgery target bone and a reference bone and a direction and distance to bend or stretch an affected part, and the like are displayed on the display screen of a bone image. The rest of the components and operations is the same as in the second embodiment. Hence, the same reference numerals denote the same components and operations, and a detailed description thereof will be omitted. Note that in this embodiment, the matching ratio is displayed as a percentage. However, any other display method such as display using a difference in the color or the length of a bar chart is usable.

Display of Matching Ratio

Figure 21:
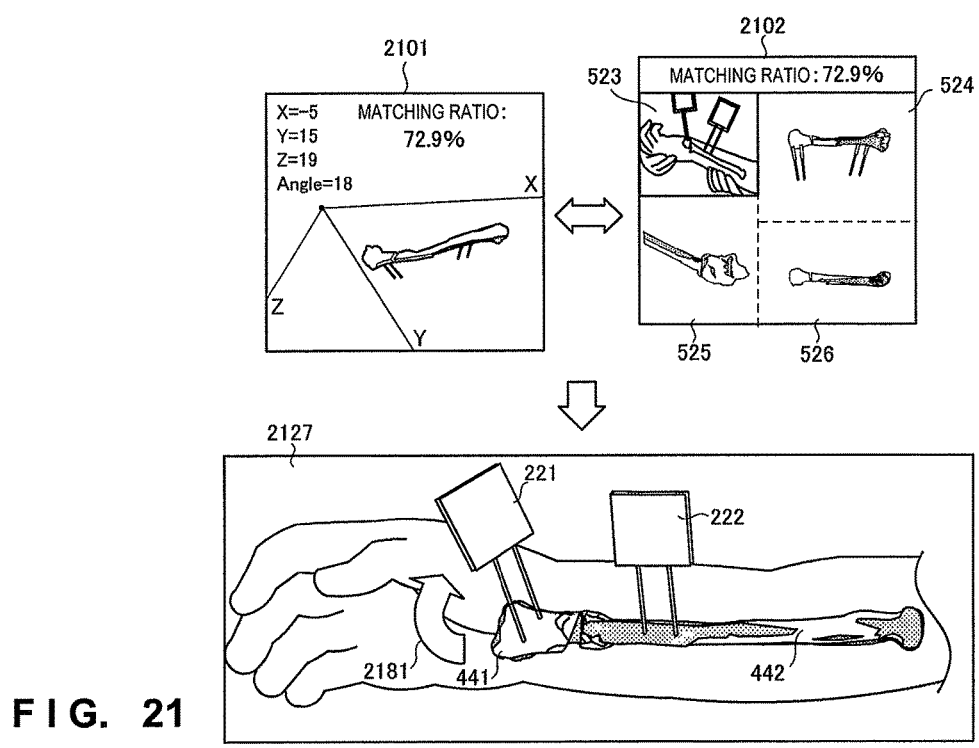
FIG. 21 is a view showing a display example of the matching ratio between a reference bone and a surgery target bone according to the fourth embodiment of the present invention.

FIG. 21 is a view showing a display example of the matching ratio between a reference bone and a surgery target bone according to this embodiment. FIG. 21 corresponds to the images 522 to 526 shown in FIG. 5B of the second embodiment.

A display screen 2101 displays the matching ratio in addition to the images of the surgery target bone and the reference bone. A display screen 2102 displays the matching ratio in addition to the images 523 to 526. Note that as the matching ratio, for example, a value obtained by multiplying the average value or maximum value of the distances of 3D bone surface data by a predetermined value is usable. However, the value is not limited to this, and various existing matching ratios are usable.

A display screen 2127 displays an arrow 2181 representing how to manipulate the affected part to appropriately overlay the surgery target bone on the reference bone. According to the example of this drawing, when the hand is bent based on the arrow 2181, correction of the affected bone can be done more easily, quickly, and properly.

According to this embodiment, it is possible to not only visually and sensibly grasp the overlay state of bone images and the overlay state of markers or pins on the display screen but also determine them by objective numerical values. Hence, the target bone can be disposed at a more appropriate position. Note that a marker position that should be may be determined in advance and displayed during surgery, and the matching ratio between the actual marker position and the displayed marker position may be displayed. A sound may be produced according to the matching ratio.

Fifth Embodiment

A surgical operation support system according to the fifth embodiment of the present invention will be described next. The surgical operation support system according to this embodiment is different from the second to fourth embodiments in that when generating preoperative preparation data, virtual 3D markers are generated on a screen and created by a 3D printer without disposing actual markers on a target bone. Note that the same reference numerals denote the same components and operations as in the above-described embodiments, and a detailed description thereof will be omitted.

Note that in this embodiment, artificial joint replacement surgery of an elbow will mainly be described. However, this embodiment is also applicable to other techniques, for example, corrective osteotomy for malunion, surgery of osteoarthritis, and the like.

Outline of Surgical Operation Support Processing

Figure 22A:
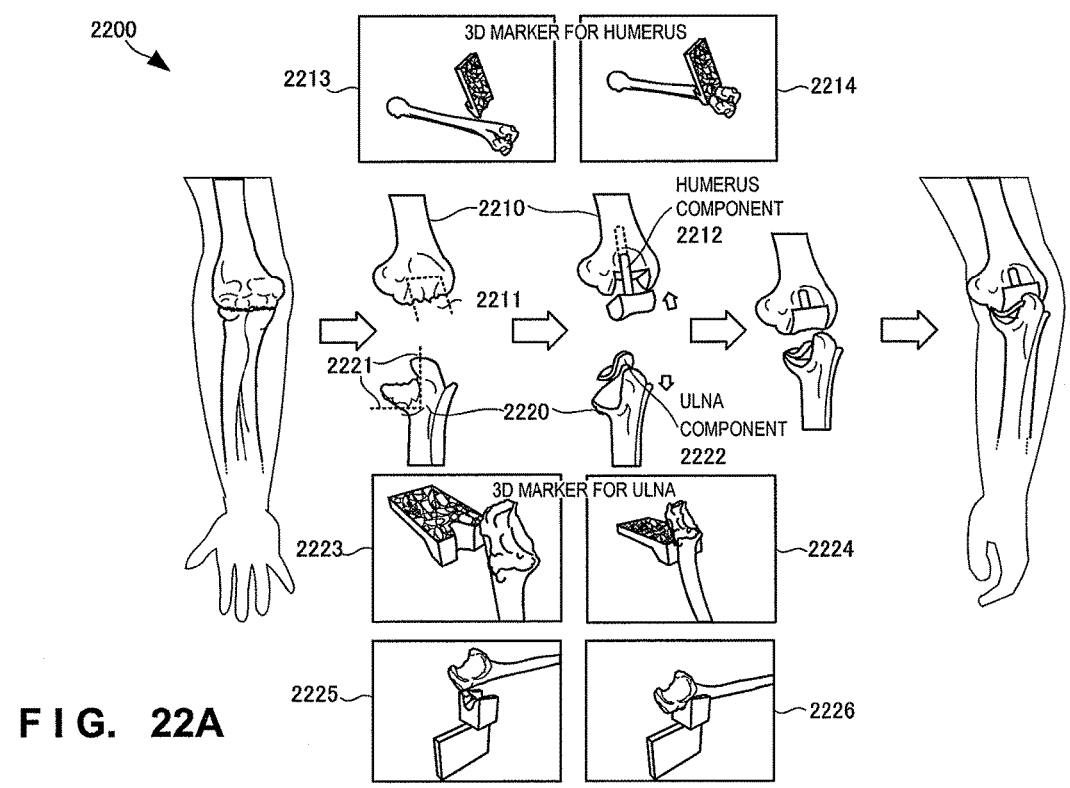
FIG. 22A is a view for explaining the outline of the processing of a surgical operation support system according to the fifth embodiment of the present invention.
Figure 22B:
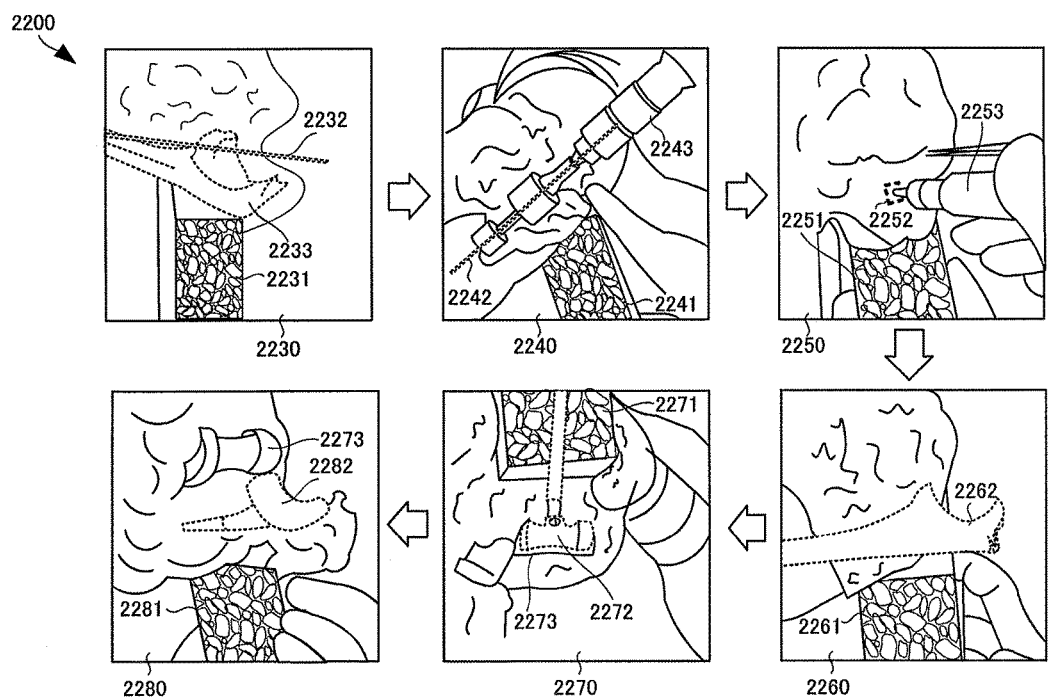
FIG. 22B is a view for explaining the outline of the processing of the surgical operation support system according to the fifth embodiment of the present invention.

FIGS. 22A and 22B are views for explaining the outline of the processing of a surgical operation support system 2200 according to this embodiment. FIG. 22A is a view showing the entire sequence of artificial joint replacement surgery. FIG. 22B is a view showing details of each processing according to this embodiment. Note that surgery of replacing the joint between the humerus and the ulna in an elbow will be described with reference to FIGS. 22A and 22B. FIGS. 22A and 22B include both a case in which the screen is the display screen of a display and a case in which the screen shows the overlay state of the display screen and a visually observed image in the optical through HMD.

Preoperative Preparation Processing

In the artificial joint replacement surgery according to this embodiment, first, CT imaging of the affected part is performed, and STL data is generated based on the CT data as preoperative preparation. While displaying the images of the humerus and the ulna by the STL data, virtual 3D markers are generated and disposed on the humerus and the ulna. Note that as for the disposing positions, each 3D marker is preferably disposed at a position near the artificial joint implantation position between the humerus and the ulna, where the 3D marker attains a characteristic shape, in a direction in which the marker surface of the 3D marker can easily be captured by a camera (the marker surface does not disappear from the visual field of the camera). Note that to facilitate image capturing by the camera, the direction of the marker surface and the base block (base) of the 3D marker placed on a bone can be changed, as shown on the lower side of FIG. 22A. At this time, the positions and directions of a bone cutting plane if bone cutting is necessary, the implant of an artificial joint to be used in this surgery, a bone surface (to be resected) to place the implant or a bone hole to fix the implant, and the like and the positions and directions of the 3D markers are set and stored in association with each other by 3D data.

Next, implants to be used are prepared, and the 3D markers are produced by a 3D printer. In addition, instruments to be used to cut a bone or resect a bone surface or instruments used to form a bone hole during surgery are prepared.

Intraoperative Processing

During surgery, the base block of the 3D marker for the humerus is placed so as to match the bone shape, as indicated by screens 2213 and 2214. The 3D marker is captured by the camera, thereby determining the position and direction of the humerus from the position and direction of the 3D marker. Bone cutting is executed while displaying a bone cutting plane 2211 of a humerus 2210 overlaid on the surgery target humerus. Next, the bone is resected while displaying the image of STL data of a humerus with a shape matching the implant overlaid on the surgery target humerus. In addition, a hole is formed in the bone while displaying a bone hole to fix the implant overlaid on the surgery target humerus. Then, a humerus component 2212 of the implant is placed.

Similarly, the base block of the 3D marker for the ulna is placed so as to match the bone shape, as indicated by screens 2223 and 2224 or screens 2225 and 2226. The 3D marker is captured by the camera, thereby determining the position and direction of the ulna from the position and direction of the 3D marker. Bone cutting is executed while displaying a bone cutting plane 2221 of an ulna 2220 overlaid on the surgery target ulna. Next, the bone is resected while displaying the image of STL data of an ulna with a shape matching the implant overlaid on the surgery target ulna. In addition, a hole is formed in the bone while displaying a bone hole to fix the implant overlaid on the surgery target ulna. Then, an ulna component 2222 of the implant is placed.

In the above-described way, each 3D marker produced by the 3D printer is placed so as to match the bone shape during surgery. This makes it possible to do surgery without forming holes in the surgery target bone of the patient and placing markers before and during surgery as in the above-described embodiment.

FIG. 22B is a view for explaining the outline of the processing of the surgical operation support system 2200 according to this embodiment. FIG. 22B shows screens according to this embodiment in each processing during artificial joint replacement surgery. Note that the 3D markers in FIG. 22B are identical. Note that FIG. 22B shows an extracted part for understanding of the embodiment and is not limited to this.

A screen 2230 is a screen when performing bone cutting of the humerus. A 3D marker 2231 placed on the humerus, a bone cutting plane 2232, and an image 2233 of STL data of the ulna are shown on the screen 2230. A screen 2240 is a screen when the bone surface is being resected for matching between the surface of the humerus and the implant to be placed. A 3D marker 2241, an instrument 2243 used to resect the bone, and a disposing plane 2242 of the instrument 2243 are shown on the screen 2240. A screen 2250 is a screen when a bone hole to fix the implant to be disposed on the humerus is being formed. A 3D marker 2251, an instrument 2253 used to form a hole, and a target position image 2252 of the bone hole are shown.

A screen 2260 shows a screen before the implant is placed on the humerus. A 3D marker 2261 and an image 2262 of STL data of the ulna are shown on the screen 2260. A screen 2270 is a screen when the implant is being placed on the humerus. A 3D marker 2271, an implant disposition image 2272, and an actual implant 2273 are shown on the screen 2270. A screen 2280 is a screen before the implant is placed on the ulna. A 3D marker 2281, the implant 2273 placed on the humerus, and an implant image 2282 to be disposed on the ulna are shown on the screen 2280.

Processing Procedure of Surgical Operation Support Processing

Figure 23:
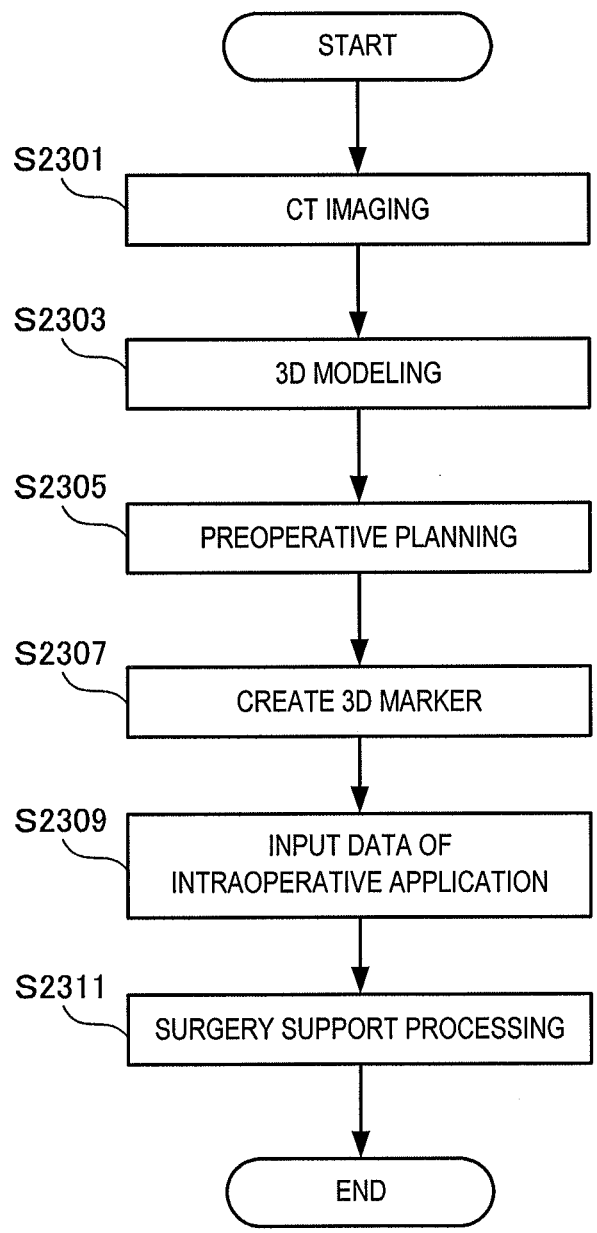
FIG. 23 is a flowchart showing the processing procedure of the surgical operation support system according to the fifth embodiment of the present invention.

FIG. 23 is a flowchart showing the processing procedure of the surgical operation support system 2200 according to this embodiment.

In step S2301, the surgical operation support system 2200 performs CT imaging of the affected part of a patient. In step S2303, the surgical operation support system 2200 forms a 3D model based on, for example, STL data. In step S2305, the surgical operation support system 2200 makes preoperative planning while displaying the 3D data. For example, a 3D marker is generated on the screen, and data to produce the 3D marker is generated. In addition, the 3D marker is associated with a surgery target bone, a bone cutting plane, a bone hole, an implant, and the like on 3D coordinates. In step S2307, the surgical operation support system 2200 produces a 3D marker having a base block matching the target bone by a 3D printer based on the data of the 3D marker.

In step S2309, the surgical operation support system 2200 inputs the processing program of an intraoperative application and each data associated with the 3D marker. In step S2311, the surgical operation support system 2200 executes surgery support based on the processing program of the intraoperative application and each data associated with the 3D marker.

Functional Arrangement of Preoperative Preparation Data Generation System

FIG. 24 is a block diagram showing the functional arrangement of an information processing apparatus 2410 in a preoperative preparation data generation system 2400 according to this embodiment. Note that the same reference numerals as in FIG. 8 denote the same functional components in FIG. 24, and a description thereof will be omitted.

As shown in FIG. 24, when capturing an affected part by a CT 321, no marker is placed on a patient 322. A bone image data generator 2411 is a functional component including the reference bone data generator 816 and the 3D data generators 817 and 818 shown in FIG. 8. A 3D marker data generator 2412 generates 3D data of a 3D marker generated based on 3D marker information input to a display/operation unit 2415. An artificial joint data generator 2413 generates 3D data of an artificial joint based on artificial joint information input to the display/operation unit 2415. Note that if an artificial joint prepared in advance is to be used, the data may be stored in an STL data DB 814 in advance. A preoperative preparation data DB 2419 stores 3D data of a surgery target bone, a bone cutting plane, a bone hole, an implant of an artificial joint, and the like in association with the 3D data of the 3D marker.

A 3D printer 2420 produces a 3D marker based on 3D printer data generated from the 3D data of the 3D marker.

3D Preoperative Preparation Image DB

FIG. 25 is a view showing the arrangement of the preoperative preparation data DB 2419 according to this embodiment. FIG. 25 shows the arrangement of preparation data planned in a technique unique to this embodiment. Note that FIG. 25 also includes the arrangement illustrated in FIG. 11.

The preoperative preparation data DB 2419 stores an affected part 2502 and a technique 2503 in association with a patient name 2501. The preoperative preparation data DB 2419 also stores a planning item 2504 necessary for the affected part 2502 and the technique 2503, and 3D data necessary for the planning item in association with a 3D marker.

Processing Procedure of Preoperative Preparation Data Generation System

Figure 26:
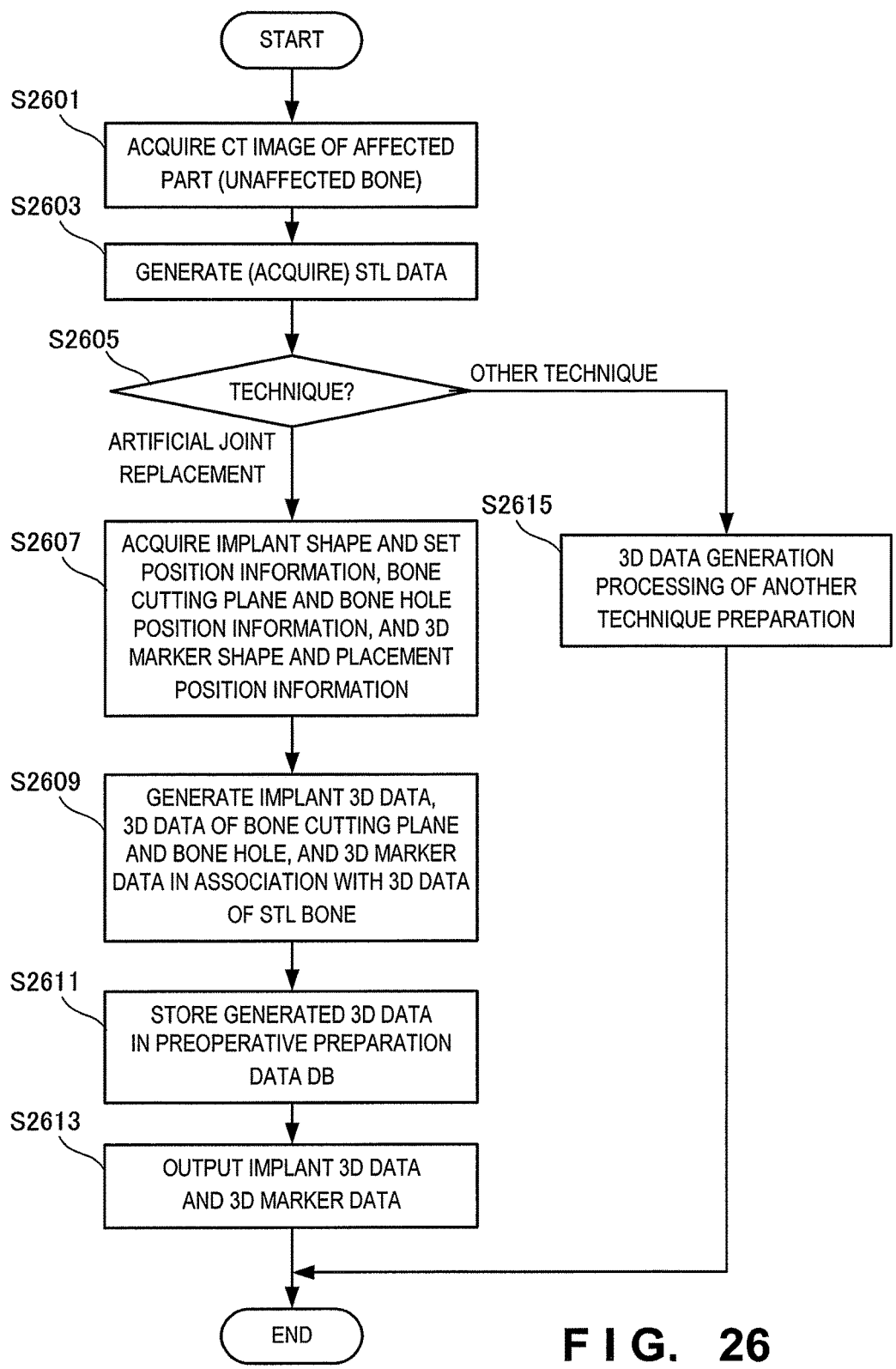
FIG. 26 is a flowchart showing the processing procedure of the information processing apparatus in the preoperative preparation data generation system according to the fifth embodiment of the present invention.

FIG. 26 is a flowchart showing the processing procedure of the information processing apparatus 2410 in the preoperative preparation data generation system 2400 according to this embodiment. This flowchart is executed by the CPU of the information processing apparatus 2410 using a RAM to implement the functional components shown in FIG. 24. Note that artificial joint replacement surgery will be described with reference to FIG. 26. However, this flowchart is also applicable to other techniques.

In step S2601, the information processing apparatus 2410 acquires a CT image of an affected part of the patient and, if necessary, a CT image of an unaffected bone. In step S2603, the information processing apparatus 2410 generates STL data from the CT image data. When requesting an external apparatus to generate STL data, the information processing apparatus 2410 acquires the STL data. In step S2605, the information processing apparatus 2410 determines the technique.

If the technique is artificial joint replacement surgery, in step S2607, the information processing apparatus 2410 acquires implant shape and set position information, bone cutting plane and bone hole position information, and 3D marker shape and set position information. In step S2609, the information processing apparatus 2410 generates implant 3D data, 3D data of the bone cutting plane and bone hole, 3D marker data, and the like in association with the 3D data of the STL bone. In step S2611, the information processing apparatus 2410 associates the generated 3D data and stores them in the preoperative preparation data DB 2419. In step S2613, when newly generating an implant, the information processing apparatus 2410 outputs the implant 3D data and also outputs the 3D marker data for the 3D printer.

If the technique is another technique in step S2605, in step S2615, the information processing apparatus 2410 generates 3D preparation data of the other technique in association with a 3D marker (for the data of other techniques, see FIG. 25).

Functional Arrangement of Intraoperative Image Processing System

FIG. 27 is a block diagram showing the functional arrangement of a tablet computer 2710 in an intraoperative image processing system 2700 according to this embodiment. The same reference numerals as in FIG. 5 or 14 denote the same functional components in FIG. 27, and a description thereof will be omitted.

The preoperative preparation data DB 2419 stores the same preparation data generated by the preoperative preparation data generation system 2400 shown in FIG. 24. A CG image generator 2714 performs 3D coordinate conversion of 3D data of the surgery target bone, the bone cutting plane, the bone hole, and the like from the preoperative preparation data DB 2419 in correspondence with the position and direction of the 3D marker from a marker analyzer 1411, thereby generating a CG image to be overlaid on a visible surgery part. A display image generator 2715 converts the image generated by the CG image generator 2714 into a display image to be displayed on a display 511, an external monitor 2720, or an HMD 2730. Note that in this embodiment, an optical see-through HMD is preferably used.

Processing Procedure of Intraoperative Image Processing System

Figure 28:
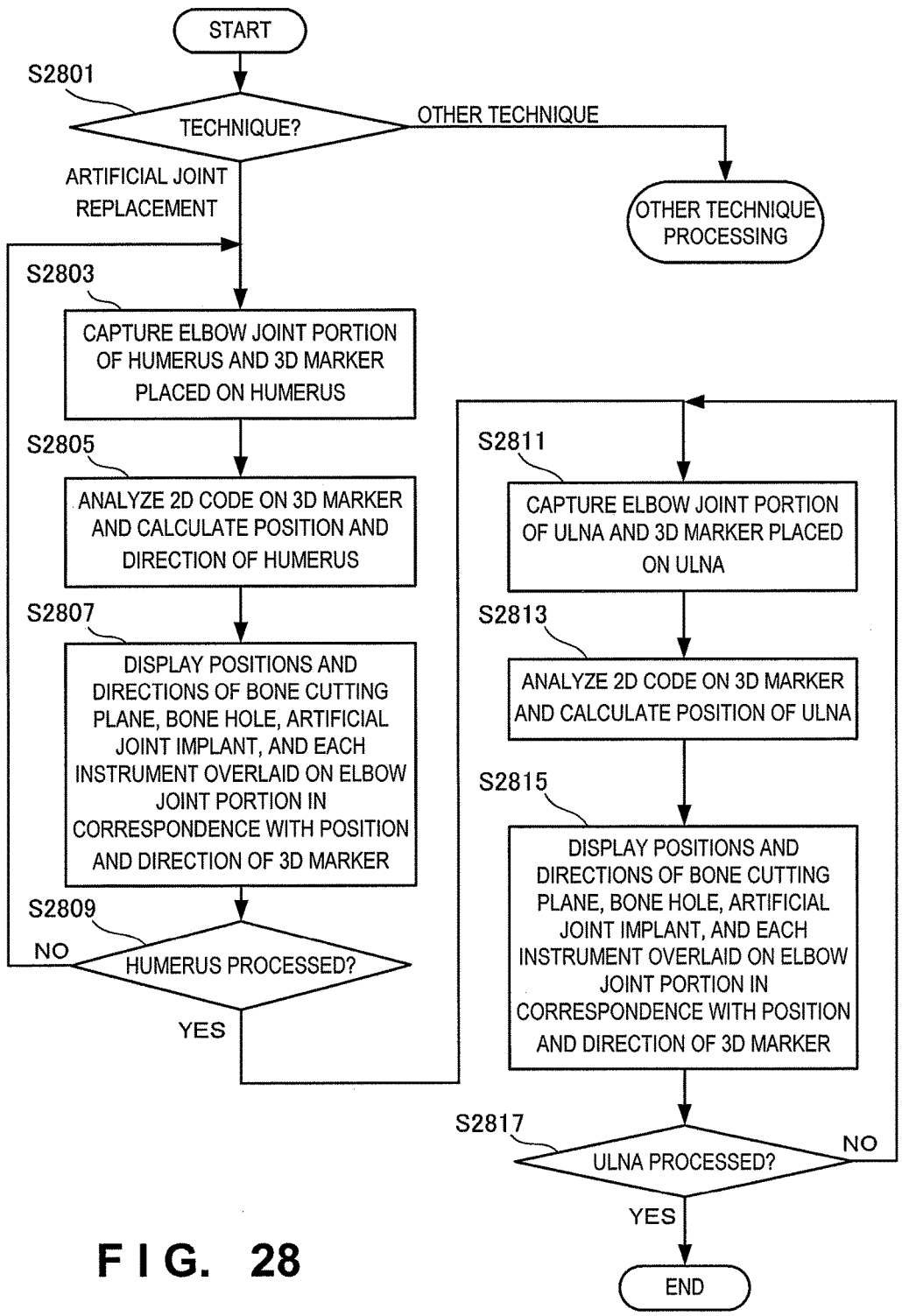
FIG. 28 is a flowchart showing the processing procedure of the tablet computer in the intraoperative image processing system according to the fifth embodiment of the present invention.

FIG. 28 is a flowchart showing the processing procedure of the tablet computer 2710 in the intraoperative image processing system 2700 according to this embodiment. This flowchart is executed by the CPU of the tablet computer 2710 shown in FIG. 27 using a RAM to implement the functional components shown in FIG. 27. Note that artificial joint replacement surgery will be described with reference to FIG. 28. However, this flowchart is also applicable to other techniques.

In step S2801, the tablet computer 2710 determines the technique. If the technique is artificial joint replacement surgery, in step S2803, the tablet computer 2710 captures the elbow joint portion of the humerus and a 3D marker produced by the 3D printer 2420 and placed on the humerus. In step S2805, the tablet computer 2710 analyzes the 2D code on the 3D marker and calculates the position and direction of the humerus. In step S2807, the tablet computer 2710 displays the positions and directions of a bone cutting plane, a bone hole, an artificial joint implant, and each instrument overlaid on the elbow joint portion in correspondence with the position and direction of the 3D marker as the surgery progresses (see FIGS. 22A and 22B). In step S2809, the tablet computer 2710 determines whether the processing of the humerus has ended. If the processing has not ended, the tablet computer 2710 returns to step S2803 to process the humerus.

In step S2811, the tablet computer 2710 captures the elbow joint portion of the ulna and a 3D marker produced by the 3D printer 2420 and placed on the ulna. In step S2813, the tablet computer 2710 analyzes the 2D code on the 3D marker and calculates the position and direction of the ulna. In step S2815, the tablet computer 2710 displays the positions and directions of a bone cutting plane, a bone hole, an artificial joint implant, and each instrument overlaid on the elbow joint portion in correspondence with the position and direction of the 3D marker as the surgery progresses (see FIGS. 22A and 22B). In step S2817, the tablet computer 2710 determines whether the processing of the ulna has ended. If the processing has not ended, the tablet computer 2710 returns to step S2811 to process the ulna.

Note that FIG. 28 illustrates performing the ulna after the processing of the humerus. However, the processes may be performed in a reverse order or progress simultaneously.

According to this embodiment, during surgery, a 3D marker produced by the 3D printer is placed so as to match the shape of a bone during surgery. This makes it possible to support surgery without forming holes in the surgery target bone of the patient and placing markers before and during surgery.

Sixth Embodiment

A surgical operation support system according to the sixth embodiment of the present invention will be described next. The surgical operation support system according to this embodiment is different from the second to fifth embodiments in that 3D data of a target bone is acquired by a depth sensor in intraoperative image processing using, as a marker, 3D data of a part in which the surgical operation of a target bone is performed. Note that the same reference numerals denote the same components and operations as in the above-described embodiments, and a detailed description thereof will be omitted.

Note that preoperative preparation data according to this embodiment is similar to that of the above-described embodiments except that separate marker information is not included because the 3D surface image of the surgery target bone is used as a marker, and a description thereof will be omitted. In the following embodiment, a case in which an HMD and a depth sensor are integrated will be described. If the HMD and the depth sensor are separated, position determination needs to be done by adding a marker to a position sensor (for example, GPS) or depth sensor.

Functional Arrangement of Intraoperative Image Processing System

FIG. 29 is a block diagram showing the functional arrangement of an information processing apparatus 2910 in an intraoperative image processing system 2900 according to this embodiment.

Note that the same reference numerals as in FIG. 14 or FIG. 20 denote the same functional components in FIG. 29, and a description thereof will be omitted.

A depth sensor & HMD 2920 includes a depth sensor and an optical see-through HMD. Note that the depth sensor and the HMD may be separate but are preferably integrated. The depth sensor is formed from an infrared projector 2921 and an infrared camera 2922, and acquires a depth image (distance image) of a surgery part during surgery. The distance image is equivalent to the 3D image of a surface.

An image receiver 2911 receives a depth image (distance image). A bone surface image collator 2912 performs collation with a characteristic surface image of a target bone image of preoperative preparation data 1419 using the depth image (distance image) as a marker. A CG image generator 1414 performs 3D coordinate conversion of the 3D data of the preoperative preparation data 1419 in correspondence with a change in the position and direction necessary for collation of the bone surface obtained from the bone surface image collator 2912, thereby generating a CG image.

A display 2923 of the depth sensor & HMD 2920 displays a display image from a right-eye HMD display data generator 2016 on a right-eye screen 2923a, and displays a display image from a left-eye HMD display data generator 2017 on a left-eye screen 2923b.

As described above, in this embodiment, the 3D image of the surgery target bone is used as a marker. This makes it possible to support surgery without separately creating a marker, as in the above-described embodiments.

Data Table of Bone Image Collator

FIG. 30 is a view showing a data table 3000 used by the bone image collator 2912 according to this embodiment. The data table 3000 collates the depth image (distance image) that the depth sensor has acquired from the surface of the surgery target bone of the affected part of the patient with the surgery target bone stored as the preoperative preparation data 1419, and determines the position and direction of the current surgery target bone.

The data table 3000 stores collated 3D bone data 3002 and a real space position and direction 3003 of the target bone determined from the collation result in association with a depth sensor image 3001. The data table 3000 stores 3D bone data 3004 and 3D data 3005 of the positions and directions of a bone cutting plane, a bone hole, an implant, and each instrument, which are obtained by 3D coordinate conversion, in correspondence with the real space position and direction 3003 of the target bone.

Processing Procedure of Intraoperative Image Processing System

FIG. 31 is a flowchart showing the processing procedure of the information processing apparatus 2910 in the intraoperative image processing system 2900 according to this embodiment. This flowchart is executed by the CPU of the information processing apparatus 2910 shown in FIG. 29 using a RAM to implement the functional components shown in FIG. 29. Note that the same step numbers as in FIG. 28 denote the same steps, and a description thereof will be omitted. Artificial joint replacement surgery will be described with reference to FIG. 31. However, this flowchart is also applicable to other techniques.

In step S3103, the information processing apparatus 2910 captures the elbow joint portion of the humerus by the depth sensor. In step S3105, the information processing apparatus 2910 performs matching between the humerus surface of the depth sensor image and stored 3D bone data of a humerus corresponding portion, and calculates the position and direction of the humerus. In step S3107, the information processing apparatus 2910 displays the positions and directions of a bone cutting plane, a bone hole, an artificial joint implant, and each instrument overlaid on the elbow joint portion in correspondence with the position and direction of the humerus. In step S3109, the information processing apparatus 2910 determines whether the processing of the humerus has ended. If the processing has not ended, the information processing apparatus 2910 returns to step S3103 to process the humerus.

In step S3111, the information processing apparatus 2910 captures the elbow joint portion of the ulna by the depth sensor. In step S3113, the information processing apparatus 2910 performs matching between the ulna surface of the depth sensor image and stored 3D bone data of an ulna corresponding portion, and calculates the position and direction of the ulna. In step S3115, the information processing apparatus 2910 displays the positions and directions of a bone cutting plane, a bone hole, an artificial joint implant, and each instrument overlaid on the elbow joint portion in correspondence with the position and direction of the ulna. In step S3117, the information processing apparatus 2910 determines whether the processing of the ulna has ended. If the processing has not ended, the information processing apparatus 2910 returns to step S3111 to process the ulna.

Note that FIG. 31 illustrates performing the ulna after the processing of the humerus. However, the processes may be performed in a reverse order or progress simultaneously.

According to this embodiment, the 3D image of the surface of the surgery target bone is used as a marker. This makes it possible to support surgery without separately creating a marker, as in the above-described embodiments.

Other Embodiments

Note that in the above embodiments, an affected part with marker instruments being fixed is captured by CT imaging. In preoperative preparation data generation processing, a set of a first target bone that is one of two divided surgery target bones and a reference bone is stored in association with a first marker, and a second target bone is stored in association with a second marker, thereby supporting determination of the disposition of the surgery target bone during surgery. However, if the fixing position of each marker instrument can accurately be determined, the marker instruments may be fixed after CT imaging or during surgery. In this case, associating the first target bone with the first marker and associating the second target bone with the second marker are performed during surgery. Instead of storing the set of the first target bone and the reference bone in association with the first marker, the first target bone and the second target bone may be matched with the reference bone during surgery. In this case, for example, during surgery, the first target bone may be matched with the reference bone, and the set of the first target bone and the reference bone may be stored in association with the first marker. After that, the second target bone may be manipulated so as to match the reference bone.

In the above embodiments, the surgical operation support system according to the present invention has been described using nonunion surgery as an example. However, the same effects as described above can be obtained by applying the system to fracture treatment, artificial joint replacement surgery, or the like. In the embodiments, a surgery target bone divided into two target bones has been described. If the surgery target bone is divided into three or more target bones, the embodiments can directly be expanded by fixing a marker to each of the separated target bones. For example, in artificial joint replacement surgery, three markers are supposed to be fixed to two bones on both sides of a joint and an artificial joint.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The present invention is applicable to a system including a plurality of devices or a single apparatus. The present invention is also applicable even when a surgical operation support program for implementing the functions of the embodiments is supplied to the system or apparatus directly or from a remote site. Hence, the present invention also incorporates a control program installed in a computer to implement the functions of the present invention by the computer, a medium storing the control program, and a WWW (World Wide Web) server that causes a user to download the control program. Especially, the present invention incorporates at least a non-transitory computer readable medium storing a control program that causes a computer to execute processing steps included in the above-described embodiments.

This application claims the benefit of Japanese Patent Application No. 2013-123209 filed on Jun. 11, 2013, which is hereby incorporated by reference herein in its entirety.

The invention claimed is:

1. A surgical operation support system comprising:
a storage that stores 3D data of target bones that undergoes a surgical operation and position data of markers in association with each other;
an image capturer that captures the markers of the target bones; and
a display that changes display of the target bones in accordance with a change in positions of the captured markers using the data stored in said storage,
wherein said storage stores 3D data of a first target bone that is one of two divided surgery target bones and 3D data of a reference bone partially overlapping the first target bone in association with position data of a first marker fixed to the first target bone, and stores 3D data of a second target bone that is another of the two divided surgery target bones in association with position data of a second marker fixed to the second target bone,
said image capturer captures the first marker fixed to the first target bone, the second marker fixed to the second target bone and an affected part of a patient incorporating the target bone, and
said display displays a bone image of the first target bone, a bone image of the reference bone, and a bone image of the second target bone, which are overlaid on an image of the affected part, in accordance with relative positions of the first marker, the second marker and the affected part using the data stored in said storage, and changes display of the first target bone and the second target bone in accordance with a change in relative positions of the first marker and the second marker using the data stored in said storage such that the second target bone partially overlaps the reference bone.

2. The surgical operation support system according to claim 1, further comprising:
a marker generator that virtually generates, on a screen, 3D markers placed on characteristic portions of the target bones; and
a data output unit that outputs data of the generated 3D markers to a 3D printer configured to create the 3D markers.

3. The surgical operation support system according to claim 1, wherein said storage stores, as the markers, 3D data of portions of the target bones that undergo the surgical operation, and
said image capturer comprises a depth sensor that captures the 3D data of the portions of the target bones that undergo the surgical operation.

4. The surgical operation support system according to claim 1, wherein the 3D data of the reference bone is mirror image data of an unaffected bone that exists at a position bilaterally symmetrical to the surgery target bone.

5. The surgical operation support system according to claim 1, wherein said display displays the bone image of the first target bone, the bone image of the second target bone, and the bone image of the reference bone such that the relative positions of the bone image of the first target bone and the bone image of the second target bone change in accordance with the change in the relative positions of the first marker and the second marker.

6. The surgical operation support system according to claim 1, further comprising a preoperative preparer that stores the 3D data of the first target bone and the 3D data of the reference bone partially overlapping the first target bone in said storage in association with the position data of the first marker, and stores the 3D data of the second target bone in said storage in association with the position data of the second marker.

7. The surgical operation support system according to claim 6, wherein said preoperative preparer stores, in said storage, target relative position data of support members of the first marker and the second marker in a state in which the first target bone and the second target bone are overlaid on the reference bone, and said display displays a target position of the support member of the second marker based on the target relative position data.

8. The surgical operation support system according to claim 1, wherein said storage stores the 3D data of the first target bone, the second target bone, and the support members acquired by performing internal image capturing in a state in which the support members of the first marker and the second marker are fixed to the first target bone and the second target bone, and the surgical operation support system further comprises a position data generator that generates the position data of the first marker to be attached to the support member based on the 3D data of the support member of the first marker stored in said storage, generates the position data of the second marker based on the 3D data of the support member of the second marker stored in said storage, and stores the position data in said storage.

9. The surgical operation support system according to claim 1, wherein said display further displays a degree of overlay between the second target bone and the reference bone.

10. The surgical operation support system according to claim 1, wherein said display includes a head mounted display.

11. The surgical operation support system according to claim 10, wherein said head mounted display comprises a binocular head mounted display, and said display generates right-eye display data and left-eye display data and performs 3D display on said binocular head mounted display.

12. A surgical operation support instrument used to fix markers to pins serving as support members of a first marker and a second marker used in a surgical operation support system of claim 1.

13. The surgical operation support system according to claim 1, wherein said display further displays a degree of overlay between the second target bone and the reference bone.

14. A surgical operation support method comprising:

storing 3D data of target bones that undergo a surgical operation and position data of markers in a storage in association with each other;

capturing the markers of the target bones; and changing display of the target bones in accordance with a change in positions of the captured markers using the data stored in the storage, wherein, in said storing step, 3D data of a first target bone that is one of two divided surgery target bones and 3D data of a reference bone partially overlapping the first target bone are stored in association with position data of a first marker fixed to the first target bone, and 3D data of a second target bone that is another of the two divided surgery target bones is stored in association with position data of a second marker fixed to the second target bone, in said capturing step, the first marker fixed to the first target bone, the second marker fixed to the second target bone and an affected part of a patient incorporating the target bone are captured, and in said changing display step, a bone image of the first target bone, a bone image of the reference bone, and a bone image of the second target bone, which are overlaid on an image of the affected part, are displayed in accordance with relative positions of the first marker, the second marker and the affected part using the data stored in said storage, and display of the first target bone and the second target bone is changed in accordance with a change in relative positions of the first marker and the second marker using the data stored in said storage such that the second target bone partially overlaps the reference bone.

15. A non-transitory computer readable medium storing a surgical operation support program that causes a computer to execute a method comprising:

storing 3D data of target bones that undergo a surgical operation and position data of markers in a storage in association with each other;

capturing the markers of the target bones; and changing display of the target bones in accordance with a change in positions of the captured markers using the data stored in the storage, wherein, in said storing step, 3D data of a first target bone that is one of two divided surgery target bones and 3D data of a reference bone partially overlapping the first target bone are stored in association with position data of a first marker fixed to the first target bone, and 3D data of a second target bone that is another of the two divided surgery target bones is stored in association with position data of a second marker fixed to the second target bone, in said capturing step, the first marker fixed to the first target bone, the second marker fixed to the second target bone and an affected part of a patient incorporating the target bone are captured, and in said changing display step, a bone image of the first target bone, a bone image of the reference bone, and a bone image of the second target bone, which are overlaid on an image of the affected part, are displayed in accordance with relative positions of the first marker, the second marker and the affected part using the data stored in said storage, and display of the first target bone and the second target bone is changed in accordance with a change in relative positions of the first marker and the second marker using the data stored in said storage such that the second target bone partially overlaps the reference bone.

* * * * *